United States Patent
Hock et al.

(10) Patent No.: US 7,296,488 B2
(45) Date of Patent: Nov. 20, 2007

(54) SYSTEM AND METHOD FOR ACCESSING FERROUS SURFACES NORMALLY ACCESSIBLE ONLY WITH SPECIAL EFFORT

(75) Inventors: Vince F. Hock, Mahomet, IL (US); Charles P. Marsh, Urbana, IL (US); Warren C. Whittaker, Pittsburgh, PA (US); Frank Robb, Middletown, DE (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/098,732

(22) Filed: Apr. 5, 2005

(65) Prior Publication Data

US 2005/0252296 A1    Nov. 17, 2005

(51) Int. Cl.
*G01N 29/26*    (2006.01)
*G01D 21/00*    (2006.01)

(52) U.S. Cl. .......................... 73/866.5; 73/618; 73/623; 73/865.8

(58) Field of Classification Search ............... 73/865.8, 73/622, 623, 866.5; 324/220, 221
See application file for complete search history.

(56) References Cited

U.S. PATENT DOCUMENTS

| | | | |
|---|---|---|---|
| 3,718,978 A | 3/1973 | Van Koevering et al. | |
| 4,675,604 A * | 6/1987 | Moyer et al. | 324/220 |
| 5,435,405 A | 7/1995 | Schempf et al. | |
| 5,473,953 A | 12/1995 | Appel | |
| 5,619,423 A | 4/1997 | Scrantz | |
| 5,623,107 A | 4/1997 | Patterson et al. | |
| 5,819,863 A | 10/1998 | Zollinger et al. | |
| 6,023,986 A | 2/2000 | Smith et al. | |
| 6,038,417 A * | 3/2000 | Nagamine et al. | 399/125 |
| 6,104,970 A * | 8/2000 | Schmidt et al. | 73/291 |
| 6,594,591 B2 * | 7/2003 | Clark et al. | 324/217 |
| 6,792,602 B2 * | 9/2004 | Lin et al. | 719/310 |
| 6,882,412 B2 * | 4/2005 | Silverman et al. | 73/864.67 |
| 2002/0166396 A1 * | 11/2002 | McGrew | 73/865.8 |

* cited by examiner

*Primary Examiner*—Hezron Williams
*Assistant Examiner*—Nashmiya Fayyaz
(74) *Attorney, Agent, or Firm*—Earl H. Baugher, Jr.

(57) ABSTRACT

A system incorporating a robot to inspect ferrous surfaces. Preferably, the robot is an articulated device having a tractor module for motive power and steering, a power module for electrical power and communications and additional motive power, and a third module for cleaning and inspection. The robot uses sensors and generates and transmits signals to a computer through a tether and receives direction from an operator via the computer and tether. The computer continuously monitors the location of the robot and supports the robot during deployment. In a specific application, the robot travels the interior of a tank on a set of magnetized wheels. Prior to inspection, the tank surface is cleaned of deposits by rotary cutters and rotary brushes on the third module. The robot obtains thickness measurements via onboard ultrasonic transducers that contact the cleaned surface. A method for implementing inspection of ferrous surfaces is also described.

20 Claims, 17 Drawing Sheets

SYSTEM AND METHOD FOR ACCESSING FERROUS SURFACES NORMALLY ACCESSIBLE ONLY WITH SPECIAL EFFORT

STATEMENT OF GOVERNMENT INTEREST

Under paragraph 1(a) of Executive Order 10096, the conditions under which this invention was made entitle the Government of the United States, as represented by the Secretary of the Army, to an undivided interest in any patent granted thereon by the United States. This invention was made in part under United States Army Construction Engineering Research Laboratory Contracts numbered DACA88-93-C-0008 and DACA88-94-C-0024. This and related patents are available for licensing. Please contact Bea Shahin at 217 373-7234 or Phillip Stewart at 601 634-4113.

RELATED INVENTIONS

Under 35 U.S.C § 121, this application claims the benefit of prior co-pending U.S. patent application Ser. No. 09/553,613, now abandoned Apparatus That Accesses a Ferrous Surface That Is Inconvenient to Access in Order to Measure and Assess the Condition Thereof, by Hock et al., filed Apr. 20, 2000, and is incorporated herein by reference.

BACKGROUND

In recent years, many tanks used for the underground storage of liquids have been made of fiber reinforced synthetic resins, and so will not rust or otherwise degrade over time. Traditionally, storage tanks were made of steel, thus these tanks can corrode to the point of perforation. Once corrosion has caused perforation, tank contents leak into the ground and gradually leach into nearby underground aquifers. Replacement or repair of these tanks to correct the damage involves extensive effort and attendant expense. In the United States, approximately 700,000 underground storage tanks are estimated to be in service. Most store petrochemicals. The U.S. Environmental Protection Agency (US EPA) enforces regulations that protect against dangers inherent in defective underground storage tanks.

40 CFR §§ 280 et seq. requires that new underground storage tanks (USTs) meet stringent standards and that all existing USTs be certified to be within specified tolerances for leak resistance integrity. Certification of existing tanks requires that the tanks in current service be inspected to determine whether they meet the applicable federal standard. Traditional methods for inspection of USTs require access into the tank by a worker to visually assess the surface. For a person to enter a UST, sometimes a portion of the earth covering a tank must be excavated and the stored liquid removed. Excavation is laborious and even after the liquid removal potentially toxic residual fumes remain in the tank, especially-in tanks storing petrochemicals.

After an UST has been inspected and certified under 40 CFR §§280 et seq., a cathodic protection system may be required to reduce subsequent tank corrosion, extend tank life, and comply with updated Federal standards.

One example of a remotely controllable, self-propelled vehicle for inspecting the interior of USTs is disclosed in U.S. Pat. No. 5,435,405 to Schempf et al. The '405 patent describes a mobile vehicle having endless drive tracks that are selectively magnetically actuated during travel on the inner surfaces of a UST. As its endless drive tracks are driven in one direction, a clutch is intermittently engaged to cause a hollow shaft to rotate to intermittently activate a magnetic circuit. The vehicle is capable of climbing a vertical wall and traveling in an inverted orientation in a ferrous structure by utilization of its magnetic tracks. It is able to enter and operate in a tank that is filled with liquid and carries a camera and an ultrasonic tester. The vehicle has its basic components enclosed in a hermetically sealed and pressurized compartments to prevent explosion of the stored liquid and to keep the liquid from seeping into the electrical and mechanical parts. It is able to communicate signals indicative of its findings to an external computer.

The '405 vehicle is equipped with acoustic means facilitating navigation within an enclosed structure containing a liquid. Calibration of the navigational system is necessary when operating in multiple fluid types since sound travels at different speeds in materials of different densities. While ultrasonic transducers used by the '405 vehicle facilitate measurement of wall thickness without determining a fixed point of reference, deployment of ultrasonic sensors alone to measure thickness to assess corrosive condition may be unreliable in an underground storage tank environment. Particular frequency readings may be affected by causes unrelated to wall thickness. For example, readings may be compromised by equipment operator produced sounds or vehicles traveling nearby. Another source of error may be unknown amounts of corrosive buildup on the tank surface. The '405 vehicle incorporates no means to remove accumulated rust or sediment before measuring wall thickness. Thus a need exists for a mobile device to travel within a liquid filled tank to measure and report actual tank wall thickness by performing the necessary tasks for making reliable measurements to include removing any corrosive buildup prior to measurement.

Further, a need exists for the remote inspection of ferrous structures other than underground storage tanks. These other structures include bridges, building frames, utility towers and the like. Select embodiments of the present invention address such applications.

DETAILED DESCRIPTION

Figure 1:
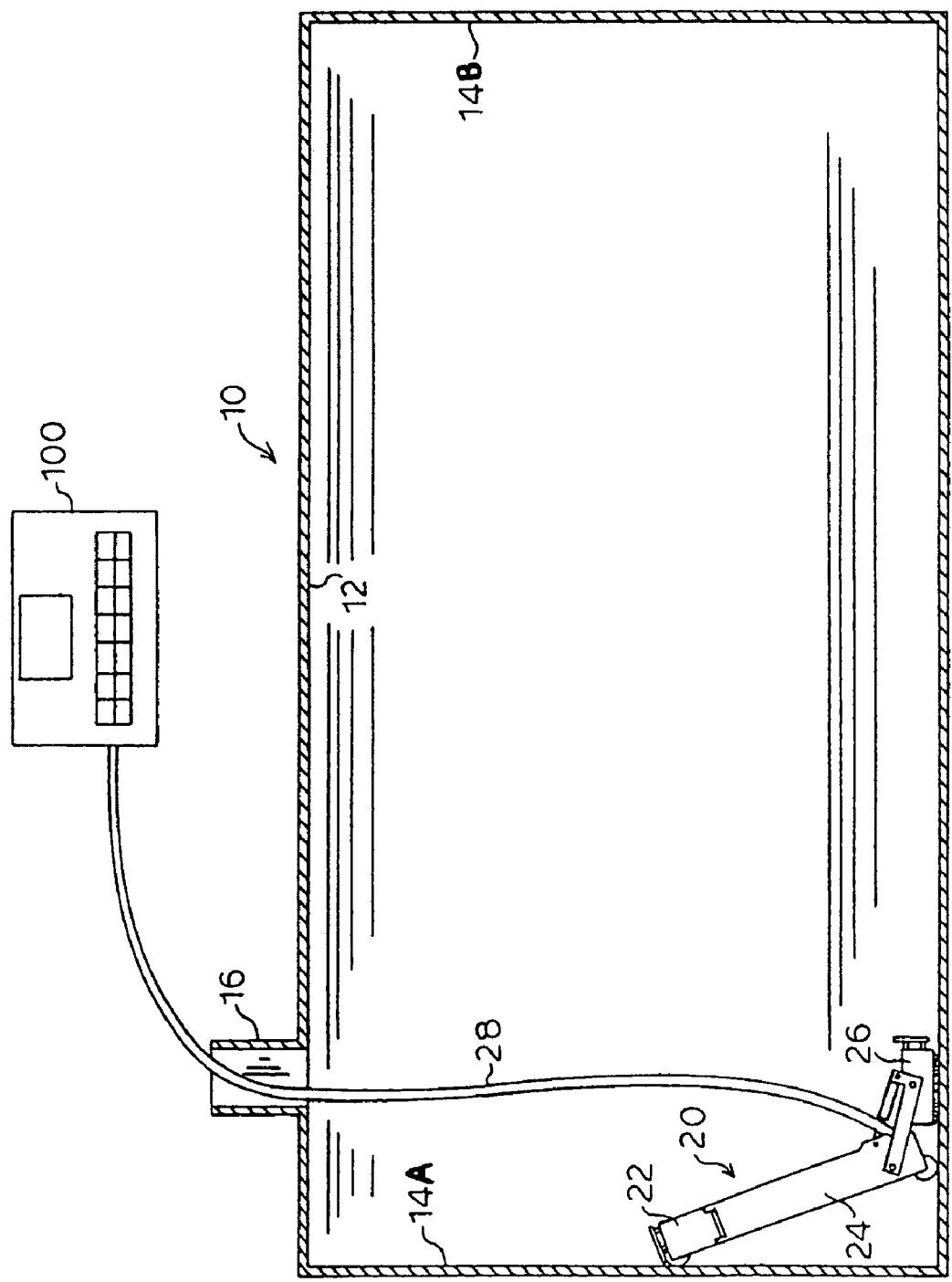
FIG. 1 is a side elevation schematic view of an embodiment of the present invention deployed within a storage tank, the tank illustrated in cross section for clarity.

In select embodiments of the present invention, a system facilitates access to ferrous surfaces of a structure for purposes such as inspection thereof. In select embodiments of the present invention, the system comprises one or more three-section conveyances having a long axis about which the sections of the conveyance move, the three sections connected in line along the long axis. In select embodiments of the present invention, the conveyance is of a size suitable for deployment upon ferrous surfaces without either modifying the structure or expanding access to the structure. The front section steers the conveyance by turning in only a first plane with respect to the middle section. The rear section is able to turn in only a second plane, the second plane being as much as fully perpendicular to the first plane in which the conveyance was being steered by the first section.

In select embodiments of the present invention, the front section incorporates a first part of a first connection assembly for connection to the middle section, one or more magnetic wheeled axle assemblies comprising polar member wheels and annular permanent magnets and one or more pivotable lever arms. The front section steers and transfers part of the power to propel the conveyance.

In select embodiments of the present invention, the middle section incorporates one or more magnetic wheeled axle assemblies comprising polar member wheels and annular permanent magnets. In select embodiments of the present invention, the middle section incorporates a second part of the first connection assembly for connection to the front section, a first part of a second connection assembly for connection to the rear section, and one or more motors incorporating interoperable connections to one or more devices in each of the front, middle and rear sections and one or more push rods.

In select embodiments of the present invention, the rear section incorporates a second part of the second connection assembly for connection to the middle section, and one or more abrading devices. In select embodiments of the present invention, the rear section may articulate to permit changing the plane of operation of the conveyance only if each of the front, middle and rear sections are approximately aligned along the centerline of the long axis of the conveyance.

In select embodiments of the present invention, the conveyance may move to a surface of operation in a plane different from the plane of the surface of current operation only in a forward direction such that the front section is moved to a new surface of operation prior to the middle and rear sections.

In select embodiments of the present invention, one or more tethers provide communication with the conveyance from external sources. In select embodiments of the present invention, a tether incorporates means for distributing power, means for distributing control signals and means for distributing fluids to the conveyance.

In select embodiments of the present invention, one or more control systems communicate with the means for distributing control signals, part of which control system is remote from the conveyance and communicating with the conveyance via the means for distributing control signals. The control system communicates with one or more power sources external to the conveyance, the power sources energizing the motors used in the conveyance and one or more sensors incorporated in the conveyance to facilitate at least navigation and inspection functions.

In select embodiments of the present invention, the conveyance may move onto a surface in a different plane only when the front section is moving in a forward direction.

In select embodiments of the present invention, the conveyance responds to input from one or more first contact switches communicating with a first pair of sensors located on the front of the front section, the sensors mounted on a first telescoping mount that is parallel to the front side of the front section, the mount compressing equally along its length upon contact with a surface that is approximately perpendicular to the direction of operation of the conveyance, the compression activating one or more first contact switches.

In select embodiments of the present invention, a second pair of sensors is mounted on a second telescoping mount that is parallel to the back of the rear section, the mount compressing upon contact in a manner similar to the front mount, the compression activating one or more second contact switches, such that activating a second contact switch alerts the conveyance to the need to alter course.

In select embodiments of the present invention, one or more of the motors is a reversible servomotor, and one or more of the reversible servomotors incorporates one or more odometric encoders.

In select embodiments of the present invention, the abrading device is selected from the group consisting of rotatable brushes, rotatable cutting wheels, scrapers, and combinations thereof, such that the rotatable brushes and rotatable cutting wheels are powered by one or more motors. In select embodiments of the present invention, scrapers are employed in pairs, mounted adjacent the outer circumference of each of the polar member wheels such that the pairs of scrapers serve to remove debris that accumulates on the polar member wheels. In select embodiments of the present invention, a first scraper in the pair is mounted to remove debris when the conveyance is moving in a first direction and a second scraper in the pair is mounted to remove debris when the conveyance is moving in a direction opposite to the first direction.

In select embodiments of the present invention, the abrading device comprises one or more first rotatable cylindrical brush coaxially mounted on the rear section to be approximately parallel to, and approximately the same width as, the wheeled axle assemblies. In select embodiments of the present invention, the abrading device comprise one or more first rotatable cylindrical cutting wheels coaxially mounted on the rear section to be approximately parallel to, and approximately the same width as, the wheeled axle assemblies such that the first cutting wheel rotates in the direction of movement of the conveyance and is protected by a unidirectional clutch. In select embodiments of the present invention, the abrading device comprises one or more cooperating pairs of abrading devices, each pair comprising a cylindrical rotatable brush and a cylindrical rotatable cutting wheel, the pair coaxially mounted across the width of the rear section so as to be parallel to the plane of operation of the conveyance and approximately the same width as the wheeled axle assemblies.

In select embodiments of the present invention, the abrading device comprises a first and second cooperating pair, the first brush and first cutting wheel of the first pair rotating upon the conveyance moving in a first direction such that the first rotating brush rotates counter to the rotation of the first cutting wheel. The second rotating brush and second cutting wheel of the second pair are rotated upon the conveyance moving in a second direction opposite to the first direction, the second rotating brush rotating counter to the second cutting wheel.

In select embodiments of the present invention, each magnetic wheeled axle assemblies comprises three or more polar member wheels of a first diameter coaxially mounted parallel one to the other on each of the wheeled axle assemblies and two or more annular permanent magnets of a second diameter smaller than the first diameter, such that each magnet is mounted coaxially so as to separate each of the polar member wheels from another of the polar member wheels and the magnets closest to each other are oriented with opposing polarities. In select embodiments of the present invention, one or more polar member wheels incorporate grooves across the width of the outer circumference of the polar member wheel, the grooves enhancing traction of the polar member wheels.

In select embodiments of the present invention, the conveyance is portable and configurable to insert into a riser of an underground tank. In select embodiments of the present invention, the conveyance weighs less than about 18 Kg (40 lbs) and is configurable to have a diameter perpendicular to the long axis thereof of less than about 10 cm (4.0 inches) to permit insertion into the riser.

In select embodiments of the present invention, the front section comprises one or more magnetic wheeled axle assemblies incorporating three or more polar member wheels and two or more magnets; a first steering mechanism for orienting the front section in a single plane such that orienting the front section in a single plane also orients the conveyance; one or more pivotally mounted first lever arms, the first lever arm operating to lift the front section from a first surface upon which the first wheeled axle assembly is resting and to lower the first wheeled axle assembly to rest upon a surface that may be different from the first surface; and first communicating assemblies that facilitate operation of the first wheeled axle assembly, the first lever arm and the steering mechanism.

In select embodiments of the present invention, the middle section comprises one or more second wheeled axle assemblies each having three or more polar member wheels and two or more magnets; one or more motors; one or more first push rods; a first part of a maneuvering assembly; second communicating assemblies communicating with some of the first communicating assemblies; third communicating assemblies communicating with the second wheeled axle assembly; and fourth communicating assemblies communicating with some parts of the middle and rear sections.

In select embodiments of the present invention, the rear section comprises one or more abrading devices; a second part of the maneuvering assembly, the maneuvering assembly permitting the rear section to follow the middle section onto a surface in a plane of operation different from a plane of operation in which the rear section is operating; one or more biasing mechanisms such that the biasing mechanisms permit the rear section to maintain firm contact with the surfaces regardless of orientation of the conveyance; and fifth communicating assemblies communicating with some of the fourth communicating assemblies to facilitate operation of the abrading device.

In select embodiments of the present invention, the tether comprises a flexible hollow conduit environmentally sealed at the juncture with the conveyance and suitable for holding material selected from the group consisting of: cables, tubes, tubular nylon core, tubular nylon filler, coaxial cable, extruded jackets, braided jackets, insulated copper wire, wire, hose, pressurized hose, and combinations thereof.

In select embodiments of the present invention, the sensors are selected from the group consisting essentially of: acoustic sensors, ultrasonic transducers, electrical sensors, piezoresistive sensors, attitude sensors, contact sensors, thickness sensors, inclinometers, mutually orthogonal inclinometers, and combinations thereof. In select embodiments of the present invention, one or more of the sensors is encapsulated in a block of dense, tough and resilient material suitable for continuously contacting the surfaces while the conveyance is moving.

In select embodiments of the present invention, the control system comprises one or more personal computers, the computers interfaced to the conveyance via a tether, such that the computers facilitate control of the conveyance, positioning of the conveyance, mapping of the surfaces, assessment of the surfaces, and defect identification and location.

In select embodiments of the present invention, a supply of pressurized inert gas is interfaced to the conveyance via the tether.

In select embodiments of the present invention, one or more power sources supplies electrical power, preferably DC power, to the conveyance via the interface to the means for supplying power within the tether.

In select embodiments of the present invention, one or more transceivers are incorporated in one or more of the sections to enable communication between the conveyance and the computer.

In select embodiments of the present invention, one or more retrieval bars are affixed to the rear section of the conveyance to facilitate recovery of the conveyance from a confined location.

In select embodiments of the present invention, one or more sections are sealed at least partly and pressurized with an inert gas.

In select embodiments of the present invention, a wheeled conveyance employs modules coupled end-to-end, the wheeled conveyance facilitating inspection of ferrous surfaces indisposed to ready access. In select embodiments of the present invention, the wheeled conveyance comprises one or more central modules for powering it; one or more front modules for steering it in its current plane of operation, the front module communicating with the central module; and one or more rear modules that abrade the surface to permit onboard sensors to take measurements of the surface, the rear module also adapted to facilitate maneuvering the wheeled conveyance onto a plane of operation different from a current plane of operation, the rear module communicating with the central module.

In select embodiments of the present invention, the front module comprises one or more first wheeled axle assemblies having a first two or more polar member wheels of a first diameter, the first polar member wheels comprising a magnetically transmissive material and one or more permanent magnets of a second diameter smaller than the first diameter, each magnet coaxially mounted between a pair of the first polar member wheels such that if more than one magnet is employed, each magnet is mounted on the first wheeled axle assembly so as to be oriented with polarity opposing that of a nearest mounted one of the magnets; a first steering mechanism to orient the front module in the current plane of operation only, such that orienting the front module orients the wheeled conveyance; one or more pivotally mounted first lever arms such that the first lever arm operates on the front module to lift and lower the front module and first communicating assemblies communicating with a portion of the central module to facilitate operation of the first wheeled axle assembly, the first lever arm and the steering mechanism.

In select embodiments of the present invention, the central module comprises one or more second wheeled axle assemblies having a second two or more polar member wheels of a first diameter, the second polar member wheels comprising a magnetically transmissive material, and one or more permanent magnets, each magnet coaxially mounted between a pair of the second polar member wheels, such that if more than one magnet is employed, each magnet is mounted on the wheeled axle assembly so as to be oriented with polarity opposing that of a nearest mounted one of the magnets; one or more motors, preferably reversing servomotors; one or more first push rods; second communicating assemblies communicating with the first communicating assemblies to facilitate operation of the first wheeled axle assembly, the first lever arm and the steering mechanism; third communicating assemblies communicating with the second wheeled axle assembly to facilitate operation thereof and fourth communicating assemblies communicating with the rear module.

In select embodiments of the present invention, the rear module comprises one or more abrading devices; one or more maneuvering assemblies, such that the maneuvering assembly permits the rear module to follow the central module onto a surface in a plane of operation different from the current plane of operation of the rear module, such that the rear module may move onto a surface in a different plane only when the wheeled conveyance is moving in a forward direction; one or more biasing mechanisms such that the biasing mechanisms permit the rear module to maintain firm contact with the surface regardless of orientation of the wheeled conveyance and fifth communicating assemblies communicating with the fourth communicating assemblies to facilitate operation of the abrading devices and the maneuvering mechanisms.

In select embodiments of the wheeled conveyance of the present invention, one or more of the motors is a reversible servomotor, preferably DC powered, and one or more servomotor incorporates one or more odometric encoders.

In select embodiments of the wheeled conveyance of the present invention, the abrading device is selected from the group consisting of rotatable brushes, rotatable cutting wheels, scrapers, and combinations thereof. In select embodiments of the wheeled conveyance of the present invention, the scrapers is employed in pairs, mounted adjacent the outer circumference of each of the polar member wheels such that the pairs of scrapers serve to remove debris that accumulates on the polar member wheels and such that a first scraper in each pair is mounted to remove debris when the wheeled conveyance is moving in a first direction and a second scraper in each pair is mounted to remove debris when the wheeled conveyance is moving in a direction opposite to the first direction.

In select embodiments of the present invention, the wheeled conveyance is provided with first and second magnetic wheeled axle assemblies, each assembly comprising three polar member wheels of a first diameter coaxially mounted parallel one to the other on each of the first and second wheeled axle assemblies, respectively, and two annular magnets, each of the two magnets coaxially mounted between a pair of polar member wheels on each of the first and second wheeled axle assemblies, the magnets having a smaller diameter than the polar member wheels as mounted on the respective wheeled axle assemblies.

In select embodiments of the present invention, the wheeled conveyance incorporates one or more polar member wheels that have grooves cut across the width of the outer circumference of the polar member wheel such that the grooves enhance traction of the polar member wheel.

In select embodiments of the present invention, the wheeled conveyance is portable and configurable to insert into a riser of an underground tank. In select embodiments of the present invention, the wheeled conveyance weighs less than about 18 Kg (40 lbs) and is configurable to have a diameter perpendicular to its long axis of less than about 10 cm (4.0 inches) to permit insertion into the riser.

In select embodiments of the wheeled conveyance of the present invention, the abrading device comprises one or more rotatable cylindrical brushes coaxially mounted on the rear module to be approximately parallel to, and approximately the same width as, the wheeled axle assembly of the rear module. In select embodiments of the wheeled conveyance of the present invention, the abrading device comprises one or more rotatable cylindrical cutting wheels coaxially mounted on the rear module to be approximately parallel to, and approximately the same width as, the wheeled axle assembly of the rear module, such that the cutting wheel rotates in the direction of movement of the wheeled conveyance and is protected by a unidirectional clutch. In select embodiments of the wheeled conveyance of the present invention, the abrading device comprises one or more cylindrical rotatable brushes and one or more cylindrical rotatable cutting wheels, such that the brushes and cutting wheels are coaxially mounted across the width of the rear module, perpendicular to the long axis and parallel to the plane of operation of the wheeled conveyance such that each brush and cutting wheel is approximately the same width as the wheeled axle assembly of the rear module.

In select embodiments of the wheeled conveyance of the present invention, the abrading device comprises a first and second rotating brush and a first and second cutting wheel, such that the first rotating brush and the first cutting wheel are rotated upon the wheeled conveyance moving in a first direction, the first rotating brush rotated counter to the rotation direction of the first cutting wheel, and the second rotating brush and the second cutting wheel are rotated upon the wheeled conveyance moving in a second direction opposite to the first direction, the second rotating brush rotated counter to the rotation direction of the second cutting wheel.

In select embodiments of the wheeled conveyance of the present invention, the sensors are selected from the group consisting essentially of: acoustic sensors, ultrasonic transducers, electrical sensors, piezoresistive sensors, attitude sensors, contact sensors, thickness sensors, inclinometers, mutually orthogonal inclinometers, and combinations thereof, such that one or more of the sensors is encapsulated in a block of dense, tough and resilient material suitable for continuously contacting the surface upon which the wheeled conveyance is moving.

In select embodiments of the wheeled conveyance of the present invention, parts of one or more of the modules are sealed and pressurized with an inert gas.

In select embodiments of the present invention, a method is provided for inspecting an interior surface of a ferrous tank. The method comprises: deploying into the tank a remotely controllable robotic vehicle employing magnetic wheeled assemblies; controlling the robotic vehicle to navigate along a selected linear path to establish the orientation and position of the robotic vehicle; providing a graphical representation of the interior surface; determining the orientation and position of the robotic vehicle; controlling the robotic vehicle to navigate a pattern that covers a major portion of the interior surface, preferably all of the surface; directing the robotic vehicle to employ one or more first sensors to measure the thickness of the tank at select intervals in the pattern; receiving signals indicative of the thickness measurements from the robotic vehicle; identifying one or more instantaneous locations of the robotic vehicle, such that the locations may be displayed on the graphical representation; comparing the signals with a predetermined thickness standard; and recording the position of the signals that indicate regions of the surface to be out of standard thickness, such that the regions may be displayed on the graphical representation.

In select embodiments of the present invention, the method of controlling the robotic vehicle to navigate the pattern comprises first directing the robotic vehicle to navigate along a line on a cylindrical surface of the tank, the cylindrical surface being parallel to the long axis of the tank, until the robotic vehicle first contacts a surface not parallel to the cylindrical surface; determining whether the first contacted surface is a first end plate of the tank; if the first contacted surface is not a first end plate, directing the robotic vehicle to circumvent the first contacted surface and further like contacted surfaces that are not a first end plate; and if a subsequent contacted surface or the first contacted surface is the first end plate, directing the robotic vehicle to reverse direction by implementing a small angular difference from the prior line of travel of the robotic vehicle; repeating the above navigation process until the entire cylindrical surface has been navigated; causing the robotic vehicle to transfer to a first end plate; directing the robotic vehicle to navigate along a line through the center of the first end plate until the robotic vehicle first contacts a first surface not parallel to the first end plate; determining whether the first contacted surface not parallel to the first end plate is the cylindrical surface; if the first contacted surface is not the cylindrical surface, directing the robotic vehicle to circumvent the first contacted surface not parallel to the first end plate and further like contacted surfaces that are not the cylindrical surface; if a subsequent contacted surface or a first contacted surface not parallel to the first end plate is the cylindrical surface, directing the robotic vehicle to reverse direction by implementing a small angular difference from the prior line of travel of the robotic vehicle; repeating the navigation process until the entire first end plate surface has been navigated; causing the robotic vehicle to transfer to the cylindrical surface; directing the robotic vehicle to navigate the cylindrical surface, now known as to configuration, until the robotic vehicle contacts the second end plate; causing the robotic vehicle to transfer to the second end plate; directing the robotic vehicle to navigate along a line through the center of the second end plate until the robotic vehicle first contacts a first surface not parallel to the second end plate; determining whether the first contacted surface not parallel to the second end plate is the cylindrical surface; if the first contacted surface is not the cylindrical surface, directing the robotic vehicle to circumvent the first contacted surface not parallel to the second end plate and further like contacted surfaces that are not the cylindrical surface; if a subsequent contacted surface or the first contacted surface not parallel to the second end plate is the cylindrical surface, directing the robotic vehicle to reverse direction by implementing a small angular difference from the prior line of travel of the robotic vehicle and repeating the navigation process employed for the first end plate until the entire second end plate surface has been navigated.

In select embodiments of the present invention, the method also permits dispensing a liquid, the liquid serving as a couplant between sensors and the tank.

In select embodiments of the present invention, the method provides one or more second sensors fixedly mounted to the front of the robotic vehicle, the second sensor facilitating determination of the location of contacted surfaces in a plane different from that plane of the surface on which the robotic vehicle is traveling.

In select embodiments of the present invention, the method of provides for a transition lever arm mounted to the robotic vehicle, the lever arm operative for lifting the first magnetic wheeled axle assembly when the robotic vehicle is transitioning from a first surface to another surface angular thereto.

In select embodiments of the present invention, the method provides for one or more scrapers mounted on the rear module and positioned so as to contact the surface to clean it.

In select embodiments of the present invention, a method is provided for inspecting ferrous surfaces of a structure, the surfaces otherwise inaccessible without employing procedures that are expensive, time consuming, dangerous, or any combination thereof. The method comprises providing one or more inspection systems, each comprising one or more articulated conveyances of a size suitable for accessing the surfaces without either modifying the structure or expanding access to the structure, each conveyance incorporating three or more sections, such that a front section turns in only a first plane with respect to a middle section and a rear section turns to only a second plane, different from the first plane, with respect to the middle section; one or more tethers for providing power and other capacity to the conveyance, such that the tether may also provide one or more sources of fluid; one or more control systems, part of the control system being remote from the conveyance and connected to the conveyance via connection means within the tether, such that the control system communicates with one or more power sources external to the conveyance, such that the power source may be used to power the conveyance and one or more sensors incorporated in each conveyance to facilitate semi-autonomous operation. In select embodiments of the present invention, the method provides for operating the above inspection system for a time period necessary to collect one or more parameters suitable to describe the condition of the surface being inspected.

FIG. 1 schematically illustrates a remotely controllable robotic vehicle 20 for inspecting and assessing the corrosive damage to an underground storage tank (UST) 10. The UST 10 comprises cylindrical wall 12, walls or end plates 14A and 14B, and a riser 16. The riser 16 is located at the top of the UST 10 and is adapted to receive liquid into the UST 10. As depicted in FIG. 1, the UST 10 and the robotic vehicle 20 are not drawn to scale for convenience of illustration. The robotic vehicle 20 is configured to enter the UST 10 through a riser 16 with a typical inside diameter of 10.2 cm. (4 inches), as further illustrated in FIG. 3A. The robotic vehicle 20 is specifically configured to enter through the riser 16 by having an elongate shape, by having its wheels tucked within the contours of its body, and by being formed in a substantially round cross section to optimize space utilization of the robotic vehicle 20. Alternatively, if the riser 16 is not of sufficient diameter, or not serviceable, for the robotic vehicle 20 to be deployed therethrough, entry would be through a manway (not shown separately) that may require excavation. Generally, it is not necessary to drain the liquid stored in the UST 10 since the components of the robotic vehicle 20 are sealed within one or more housings and the electrical power supplied through a tether 28 by a power source (not shown separately) is considered to be safe if provided at not more than 24 volts DC. In select embodiments of the present invention, the robotic vehicle 20 receives power from and communicates with a computer 100 through the tether 28. In select embodiments of the present invention, the tether 28 (shown and described in detail in connection with FIG. 10) includes power and communication wires and fluid transmitting tubes. In select embodiments of the present invention, connections are made to individual components for such purposes as power transmission and communication. In select embodiments of the present invention, such connections are made to a computer 100 that may be programmed for automatic operation or manual control of the robotic vehicle 20.

Figure 8A:
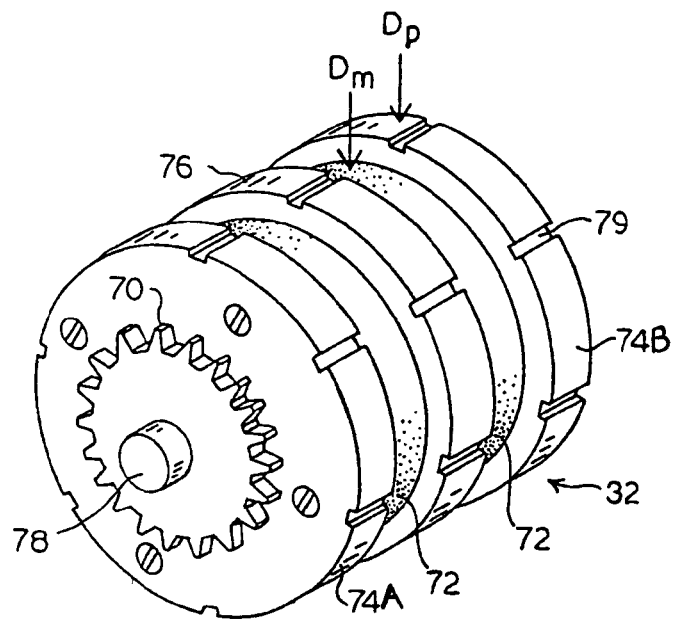
FIG. 8A is a perspective view of a magnetic wheeled axle assembly of an embodiment of the present invention.

Refer to FIG. 1. In select embodiments of the present invention, to accommodate the need to traverse and inspect the interior surface of the UST 10, the robotic vehicle 20 is constructed in three pivotally connected and articulated modules 22, 24, 26, each adapted for a specialized function. The lead or forward module, hereafter identified as tractor 22, is attached to and followed by a power module 24. The power module 24 is connected to and followed by a cleaning and inspection module 26. In FIG. 1, the robotic vehicle 20 is shown in transition from the interior surface of a cylindrical wall 12 upwards onto the interior surface of an end plate 14A. Travel of the robotic vehicle 20 within the UST 10 is enabled by use of motor driven magnetic wheeled axle assemblies as shown in FIG. 8A.

Figure 2A:
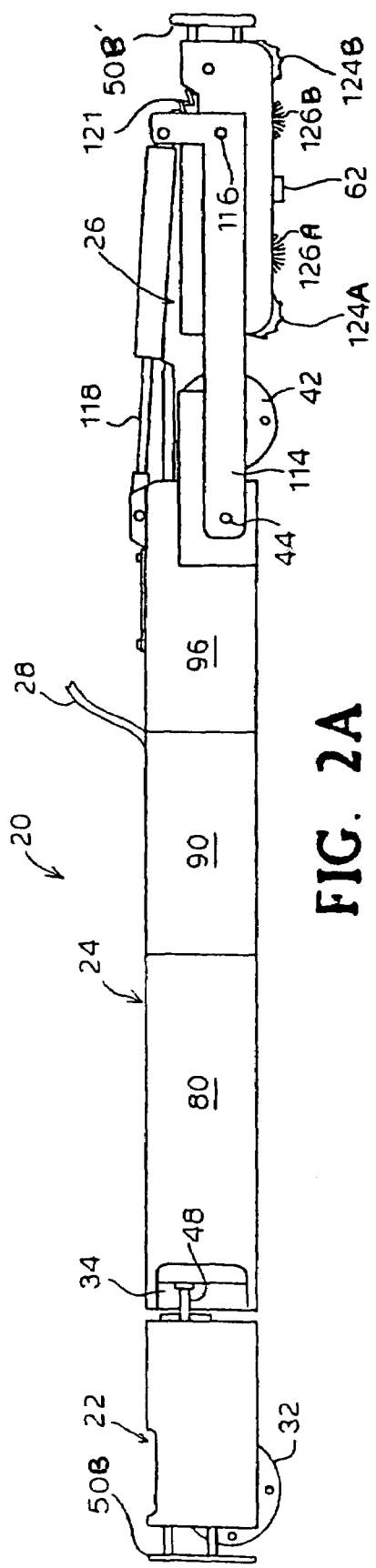
FIG. 2A is a side elevation view of the three modules of an embodiment of the present invention.
Figure 2B:
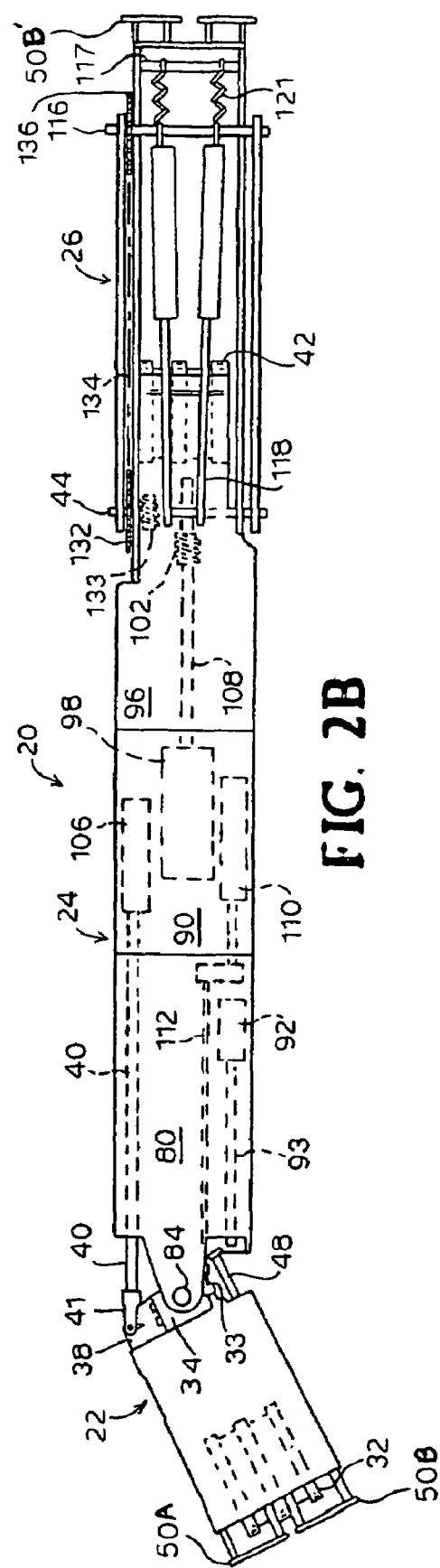
FIG. 2B is a top plan view of the embodiment of FIG. 2A with the first module of the embodiment pivoted at an angle to the second and third modules.

Refer to FIGS. 2A and 2B, showing the robotic vehicle 20 in side elevation and top plan views, respectively. As illustrated in FIGS. 2A and 2B, the robotic vehicle 20 may be deployed both vertically and horizontally. For example, the cleaning and inspection module 26 is designed to pivot in either an upward or downward direction only. The tractor module 22 is designed to pivot only laterally to the left or right. Since the robotic vehicle 20 is operative in various orientations, e.g., horizontal mode with wheels facing down, inverted horizontal mode with wheels facing up, and vertical mode as occurs on the end plates 14A, 14B; relative movement of the robotic vehicle 20 will be described from the perspective of the horizontal mode with wheels facing down unless otherwise noted. In the horizontal mode, the horizontal plane is referred to as the X-Z plane, and its two mutually orthogonal vertical planes are the X-Y and Z-Y planes. Sealing of the housing of the robotic vehicle 20 against leakage is accomplished by use of an RTV silicone compound between stationary parts and with O-rings for sealing shafts that move through housing walls. Once the housing of the robotic vehicle 20 is sealed, a pressurized gas, such as air or nitrogen, is introduced to the interior of the housing to prevent seepage of liquid into the housing. The tractor module 22 is flexibly assembled and connected to the power module 24 by a vertical front pivot joint 34 including a pin 84. This arrangement facilitates angular flexure between the tractor module 22 and the power module 24 only in the X-Z plane. The cleaning and inspection module 26 is assembled and connected to the power module 24 by a horizontal rear pivot joint 44. The rear pivot joint 44 enables angular flexure between the power module 24 and the cleaning and inspection module 26 only in the vertical planes X-Y and Z-Y.

Refer to FIG. 2B illustrating the power module 24 as constructed with a forward segment 80, a middle segment 90, and a rear segment 96. In select embodiments of the present invention, electrically energized, reversible motors 92 and 110 drive various functions in the robotic vehicle 20. FIG. 2B shows the connections of these motors 92, 110 to tractor 22 and cleaning and inspecting module 26. The middle segment 90 contains the motor 110 that generates and transmits drive power to the front magnetized wheeled axle assembly 32. Power is transmitted from the motor 110 to the magnetized wheeled axle assembly 32 by means of a drive shaft 112. In select embodiments of the present invention, the drive shaft 112 includes a telescoping universal joint (not shown separately) at its transition to a drive mechanism housed in the tractor module 22. The forward end of the shaft 112 connects to a gear reducer 30 (see FIG. 3B) located in the tractor module 22. In select embodiments of the present invention, the gear reducer 30 drives the front magnetized wheeled axle assembly 32 through the chain 31 and the sprocket 70 depicted in FIG. 3B. In select embodiments of the present invention, the motor 92 (see FIG. 2B) and other electric apparatus in the body of the robotic vehicle 20 are powered at 24 volts DC. Use of DC power permits reversing the direction of drive without the added circuitry typically required with use of AC motors. In select embodiments of the present invention, small, reversible, high-speed electric motors are used in conjunction with worm and wheel type gear reducers (not shown separately) to conserve space. Typically, in select embodiments of the present invention, the worm and wheel type gear reducers are each immersed in an oil bath. In select embodiments of the present invention, the electric motors 92, 110 that drive the robotic vehicle 20 meet the design specification requirement of 30 lbf. of power per wheel 32, based on a system force balance analysis.

Refer to FIG. 2B. In select embodiments of the present invention, a shaft 40 is actuated to pivot the tractor module 22 laterally about pin 84 relative to the power module 24 to accomplish steering. In select embodiments of the present invention, the shaft 40 is moved linearly by a linear actuator (not shown separately) formed by the lead screw motor 106. In select embodiments of the present invention, the shaft 40 is configured to pass to the front end of the power module 24 and connect to the coupling 38 on the tractor module 22, thereby causing the tractor module 22 to change its direction of travel.

The middle segment 90 of the power module 24 houses a reversible, electric motor 98 that supplies power through a worm and wheel gear reducer 102 (in the rear segment 96) to the rear magnetized wheeled axle assembly 42. Via the reducer 102, the rear magnetized wheeled axle assembly 42 is caused to rotate at the same speed and in the same direction as the forward magnetized wheel axle assembly 32. An incremental encoder (not shown separately) having a digital output communicates with the rear wheel drive motor 98 to obtain odometric data. In some applications of select embodiments of the present invention, a degree of slippage between the magnetized wheel asemblies 32, 42 and the surface of operation may occur, thus affecting the odometer reading. Thus, position verification may be accomplished by an operator (not shown separately) or by a computer 100 when the robotic vehicle 20 contacts a known fixed object, e.g., within the UST 10 this may be an end wall 14A, B. Thus, the occurrence of slippage does not preclude maintaining reasonably accurate real-time information regarding the position of the robotic vehicle 20. Another encoder (not shown separately), operable in a manner similar to that of the first encoder, may communicate with the drive for the front magnetized wheeled axle assembly 32, thereby improving reported positional accuracy.

Figure 6:
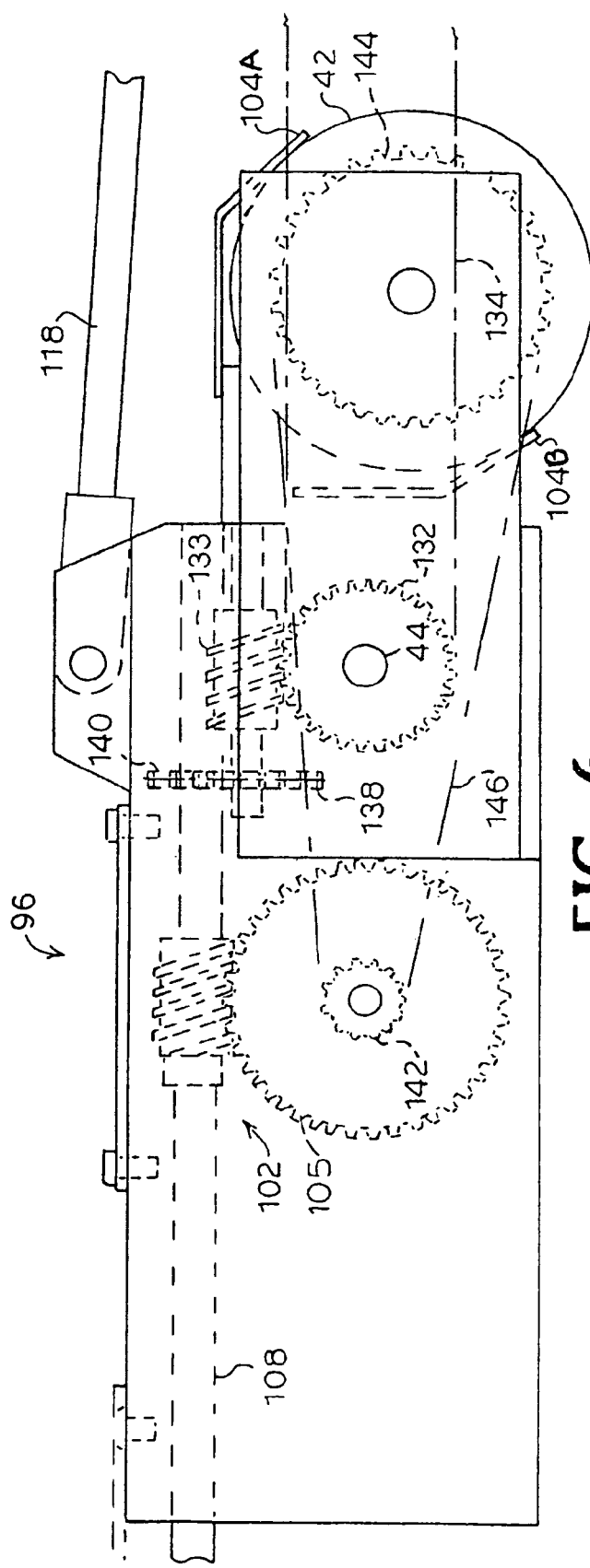
FIG. 6 is a side elevation view of a third segment of the second module of FIG. 2A depicting a rear magnetic drive wheeled axle assembly.

Refer to FIGS. 2B and 6. The motor 98 drives a shaft 108 that communicates with a gear reducer 133 that drives a sprocket 132 through a worm wheel (not shown separately) mounted on the pivot shaft 44. A chain 134 connects the drive sprocket 132 to drive the sprocket 136.

Figure 3A:
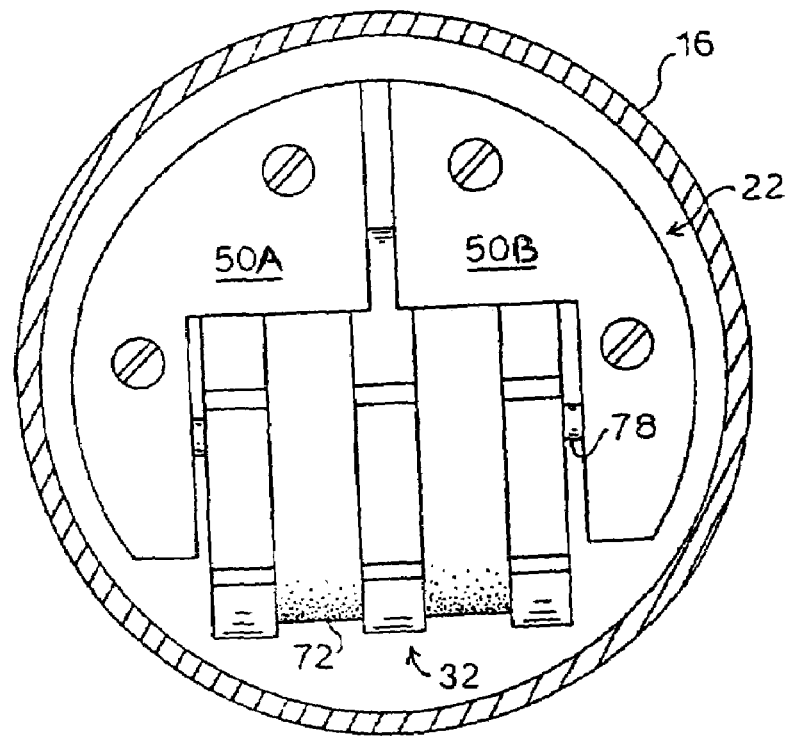
FIG. 3A is a front elevation view of the leading end of the first module of the embodiment of FIG. 2A, shown within a cross section of a riser.
Figure 3B:
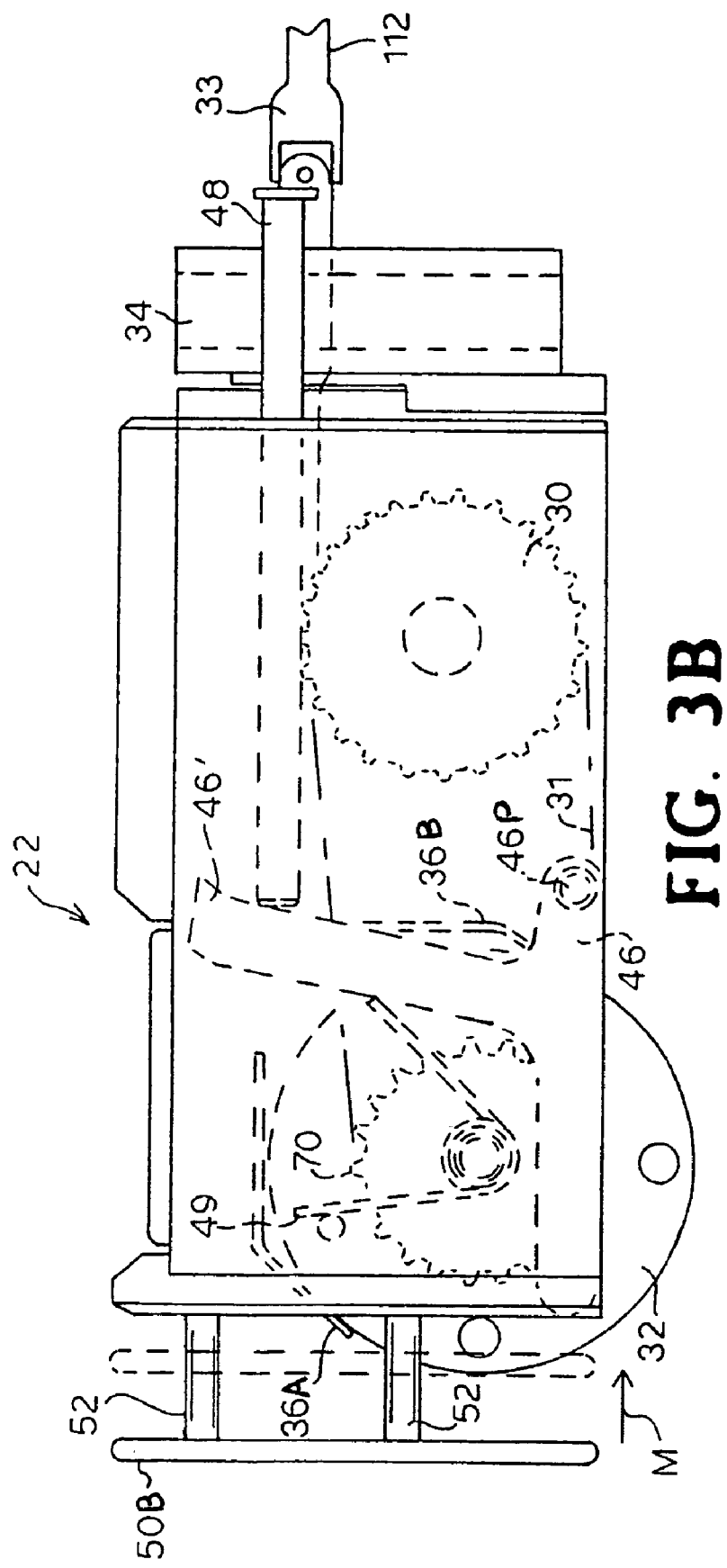
FIG. 3B is a side elevation view of the first module of the embodiment of FIG. 2A showing a front magnetic drive wheeled axle assembly and a lift apparatus in its idle orientation.
Figure 3C:
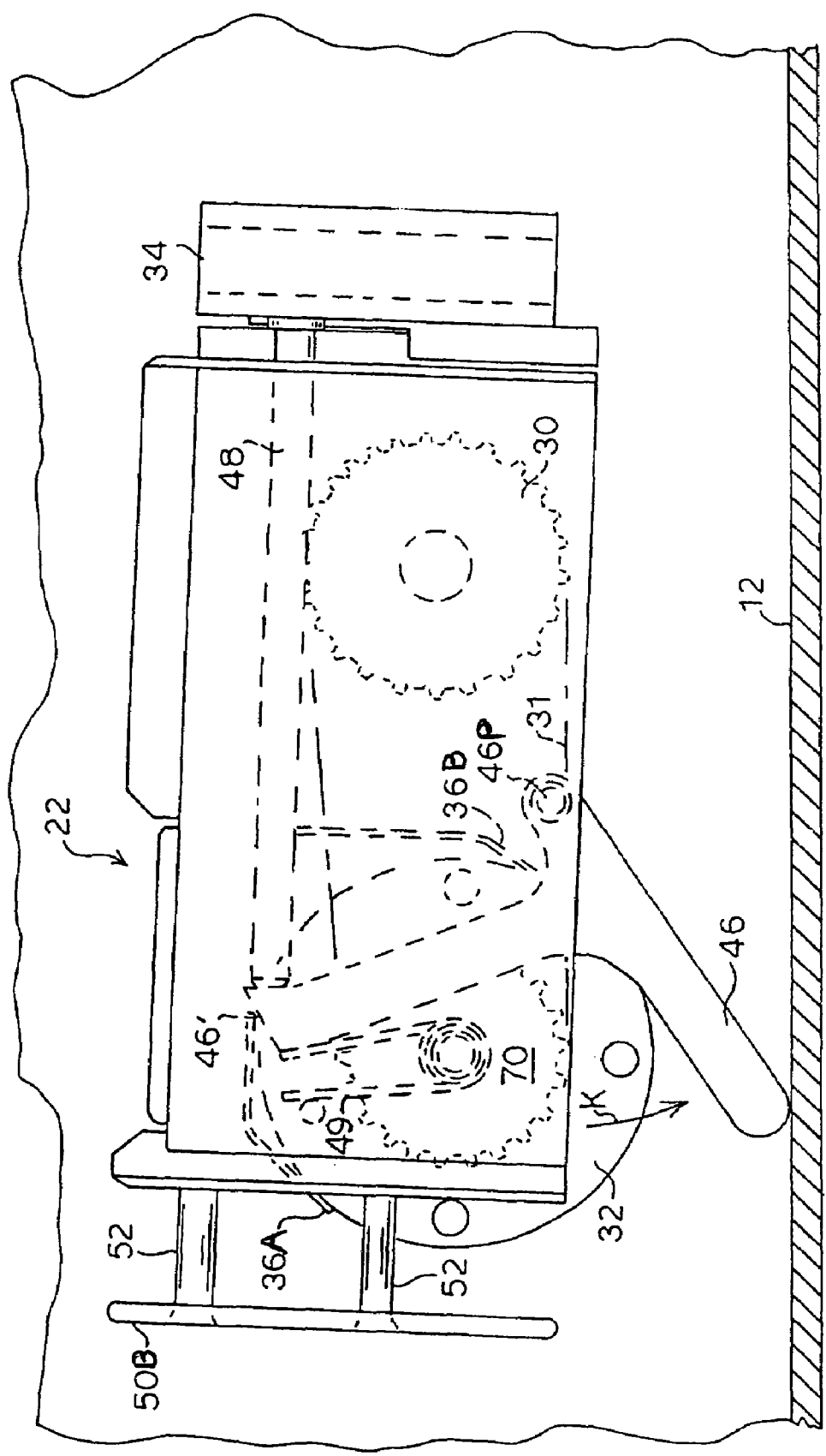
FIG. 3C depicts the module of FIG. 3B with the lift apparatus in its lifting orientation.

Refer to FIGS. 2B, 3B, C, and 7. The sprocket 136 is mounted to provide power to the rotary cutters 124A, B and brushes 126 A, B of the cleaning and inspection module 26. The motor 92 is housed in the forward segment 80 for supplying linear power to the lead screw 93. The lead screw 93 operates linearly to contact and move the push rod 48, in turn, causing the transition lever arm 46 to pivot so as to lift the front end of the tractor module 22 as depicted in FIG. 3C. The lead screw 93 is aligned with the push rod 48 when the tractor module 22 is aligned with the power module 24.

In summary, the drive motors are: the motor 92 to drive the front magnetized wheeled axle assembly 32; the motor 98 to drive the rear magnetized wheeled axle assembly 42 and the cutters 124A, B and brushes 126A, B of cleaning and inspection module 26; the motor 106 to drive the steering function of the tractor module 22; and the motor 110 to activate the lifting function of the transition lever arm 46 and the rear push rod 137.

Refer to FIGS. 3A, B, C. The tractor module 22 includes the front magnetized drive wheeled axle assembly 32 that is driven by a two-stage reduction drive. The front drive wheeled axle assembly 32 is mounted to the tractor module 22 far forward so as to protrude from the body of the tractor module 22 in a forward direction of travel. The front drive wheeled axle assembly 32 is also tucked within the substantially round body of the robotic vehicle 20 to limit the cross sectional size thereof to enable entry through a riser 16 as shown in FIG. 1. Typical risers have a diameter of four inches. As the front magnetized wheeled axle assembly 32 moves along the surface of the UST 10, loose particles of oxidized iron (rust) adhere to the contacting surfaces of the front magnetized wheeled axle assembly 32. Thus, in select embodiments of the present invention, a pair of scrapers 36A, B, preferably of a corrosion resistant material such as stainless steel, are mounted on the body of the tractor module 22 so that an edge of each presses against the cylindrical surface of the drive wheels 74A, B, 76 of the front magnetic wheeled axle assembly 32, dislodging particles that accumulate thereon. The scrapers 36A, B are mounted to permit dislodging when the robotic vehicle 20 is operating in either direction. As shown in FIG. 2B, the directional rod 40 that connects to the coupling 38 through the clevis 41 operates to turn the tractor module 22 in the plane of travel only. A shaft 40 communicates linearly with the power module 24 in a direction parallel to the long axis of the power module 24 to cause the tractor module 22 to pivot about the pivot joint 34. A coupling 38, preferably formed with a slot that is substantially perpendicular to the long axis of the tractor module 22, permits the shaft 40 to move without restriction.

Refer to FIGS. 3A, B, C, depicting a pair of contact sensors, 50A, B mounted on the front left and right front corners of the tractor module 22. Each contact sensor 50A, B communicates with a contact switch (not shown separately), preferably digital, that generates a signal in response to the leading outer surface of either contact sensor 50A, B contacting something. The contact sensors 50A, B are mounted on the telescoping supports 52 configured to collapse into the tractor module 22 upon a corresponding sensor 50A, B contacting something. The degree of telescoping allows the front magnetized drive wheeled axle assembly 32 to touch and magnetically grip a surface perpendicular to the surface on which the robotic vehicle 20 is traveling prior to contact. Contact by both sensors 50A, B simultaneously is interpreted by the computer 100 as a contact with a perpendicular surface. Contact by only one of the sensors 50A, B indicates a less than perpendicular relationship between robotic vehicle 20 and the contacted surface. In select embodiments of the present invention, maximum adhesive force for the front magnetized drive wheeled axle assembly 32 is achieved by contact with the surface along a tangent across the face and parallel to the axis of the drive wheeled axle assembly 32. Thus, it is preferred that the tractor module 22 contacts the surface for transition, e.g., transition from a cylindrical wall 12 to and end plate 14A, perpendicularly. With the initial data from the contact sensors 50A, B as to the relative angle of contact of the tractor module 22, correction is made through program control by the computer 100 to achieve perpendicular approach. Attaining perpendicularity is accomplished by moving the robotic vehicle 20 backwards from the contacted surface and making additional approaches to achieve approximately simultaneous contact by sensors 50A, B.

Figure 4:
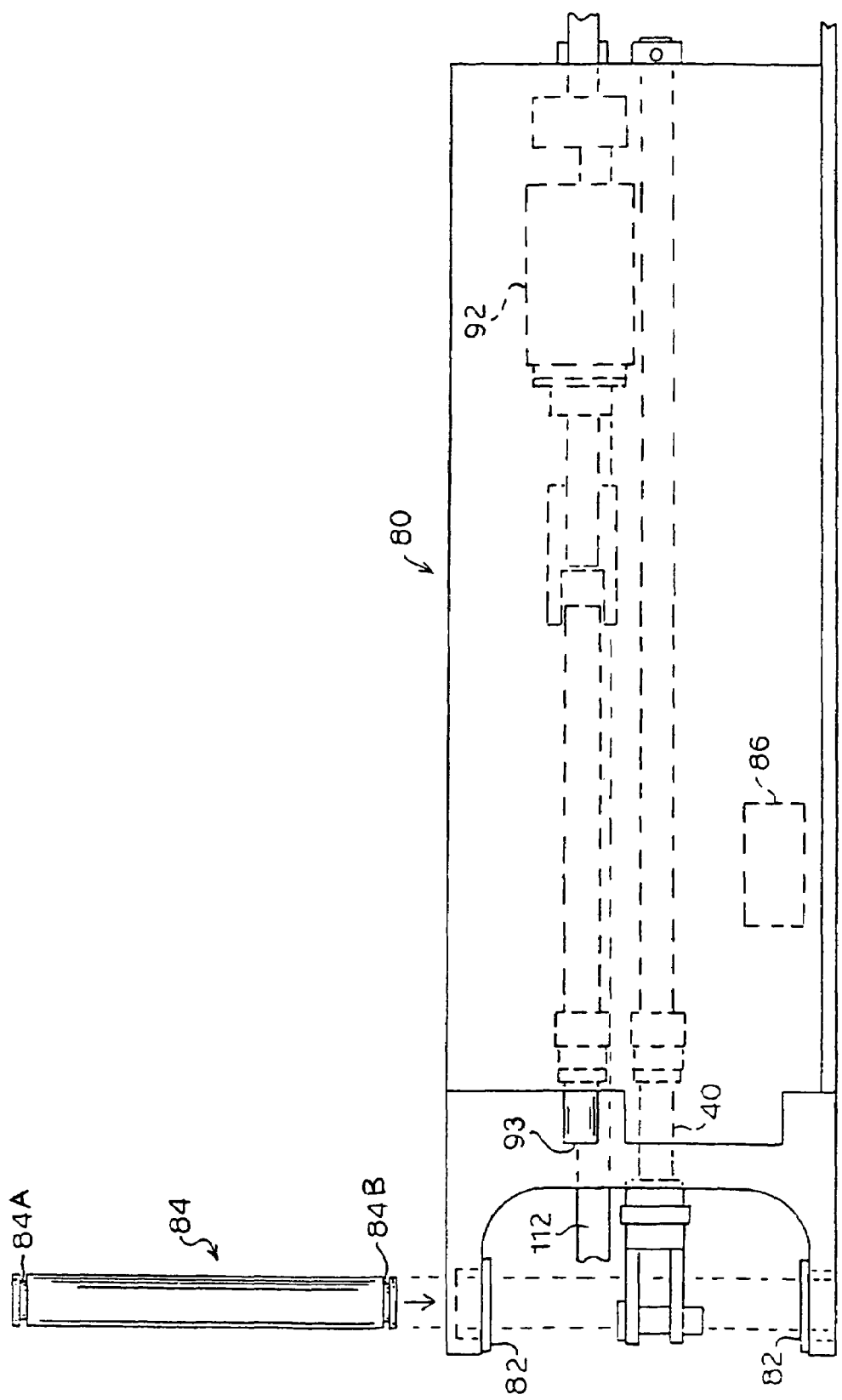
FIG. 4 is a side elevation view of a first segment of the second module of FIG. 2A showing the orientation and position determination apparatus and an exploded view of the power module pin.

Refer FIGS. 3B, C. For the robotic vehicle 20 to perform a transition from one surface to another approximately perpendicularly disposed, it is necessary to first separate the drive wheeled axle assembly 32 from the current surface of travel. Separation is accomplished by actuation of the transition lever arm 46 pivotally mounted at the pivot 46. Alternate mechanisms, such as a linearly actuated push rod also accomplish this function. The transition lever arm 46 is L-shaped, with its upper end 46' positioned adjacent the forward end of the push rod 48. As the lead screw 93 (FIG. 4) pushes against the push rod 48, the push rod 48 moves left (FIG. 3C). The actuation of the push rod 48 from its retracted position (FIG. 3B) to its extended position (FIG. 3C) forces the transition lever arm 46 to pivot about the pin 46P counterclockwise as shown by the arrow K. The downward force of the transition lever arm 46 lifts the front of the tractor module 22 so as to separate the front magnetized drive wheeled axle assembly 32 from the surface of the UST 10. When the push rod 48 retracts, the cam 46 pivots back to its initial position with the aid of a biasing means, such as a spring 49 or the like. The push rod 48 is slidingly mounted in bearings (not shown separately) in the wall of the tractor module 22 and not physically connected to the lead screw 93 (FIG. 4). When the tractor module 22 is at an angle to the power module 24, as in FIG. 2B, the push rod 48 is at a similar angle and not aligned with the lead screw 93. Thus, it is necessary to put the tractor module 22 and the power module 24 in substantial alignment prior to actuating the transition lever arm 46. As seen in FIG. 6, a solenoid-actuated push rod 137 is positioned to lift the rear magnetized drive wheeled axle assembly 42 in a manner similar to the way that the front magnetized drive wheeled axle assembly 32 is lifted.

Figure 8B:
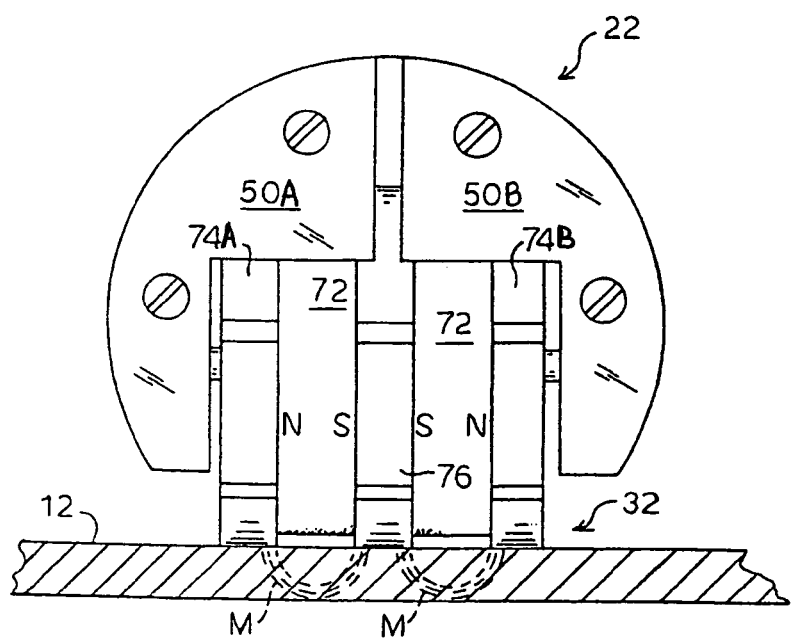
FIG. 8B is a front elevation view of the front of the first module of FIG. 2A showing the magnetized wheel in contact with a portion of a ferrous surface with dashed lines depicting lines of magnetic flux.

Refer to FIG. 8A illustrating the axial configuration of the front magnetized drive wheeled axle assembly 32. The front magnetized drive wheeled axle assembly 32 is an assembly of five disk-like members 72, 74A, B, 76 interspersed axially along a shaft 78. The outer polar members 74A, B are located toward the ends of the shaft 78, respectively and the inner polar member 76 is centrally located along the shaft 78. The polar members 74A, B, 76 are made of magnetically transmissive material, not adapted to permanently retain significant magnetic properties, such as a low carbon steel. Between each of the outer polar members 74A, B and the inner polar member 76 is an axially polar magnetic member 72, each formed of a permanently magnetic material. In select embodiments of the present invention, the axial magnetic members 72 are formed of rare earth materials, e.g., neodymium iron, and oriented such that their poles are opposite to one another, as illustrated in FIG. 8B. In this arrangement, magnetic flux M is radiated between magnetic members 72 through polar members 74A, B, 76 to establish a strong magnetic bond between the robotic vehicle 20 and the ferrous surface upon which it operates. The shaft 78 passes through the five members 72, 74A, B, 76 and mounts the sprocket 70 to receive drive power from the chain 31. The rear drive wheeled axle assembly 42 is constructed similarly.

Refer to FIG. 8A. Due to the irregular interior surface of a typical UST 10 and the frequent occurrence of lumps, select embodiments of the present invention employ a tread pattern to improve traction of the magnetized drive wheeled axle assemblies 32, 42. Multiple grooves 79 are formed on the outer periphery of each polar member 74A, B, 76 in a direction approximately parallel to the shaft 78. In one embodiment of the present invention there are six grooves 79 uniformly dispersed around each polar member 74A, B, 76. In select embodiments of the present invention, the grooves 79 may be aligned one to another across the face of the three polar members 74A,B, 76, although a non-aligned pattern is also suitable.

Refer to FIGS. 8A, B. Each polar member 74A, B, 76 is formed with a relatively large diameter $D_p$ and each magnetic member 72 with a relatively small diameter $D_m$. The pattern of magnetic flux M is shown schematically as dashed lines from each magnetic member 72 through respective polar members 74A, B, 76 to a ferrous surface such as the tank wall 12. This configuration enhances the flux pattern by causing it to intensify through the polar members 74A, B, 76. In addition, the large diameter polar members 74A, B, 76 protect the smaller diameter magnetic members 72 from damage due to wear or impact.

Figure 9A:
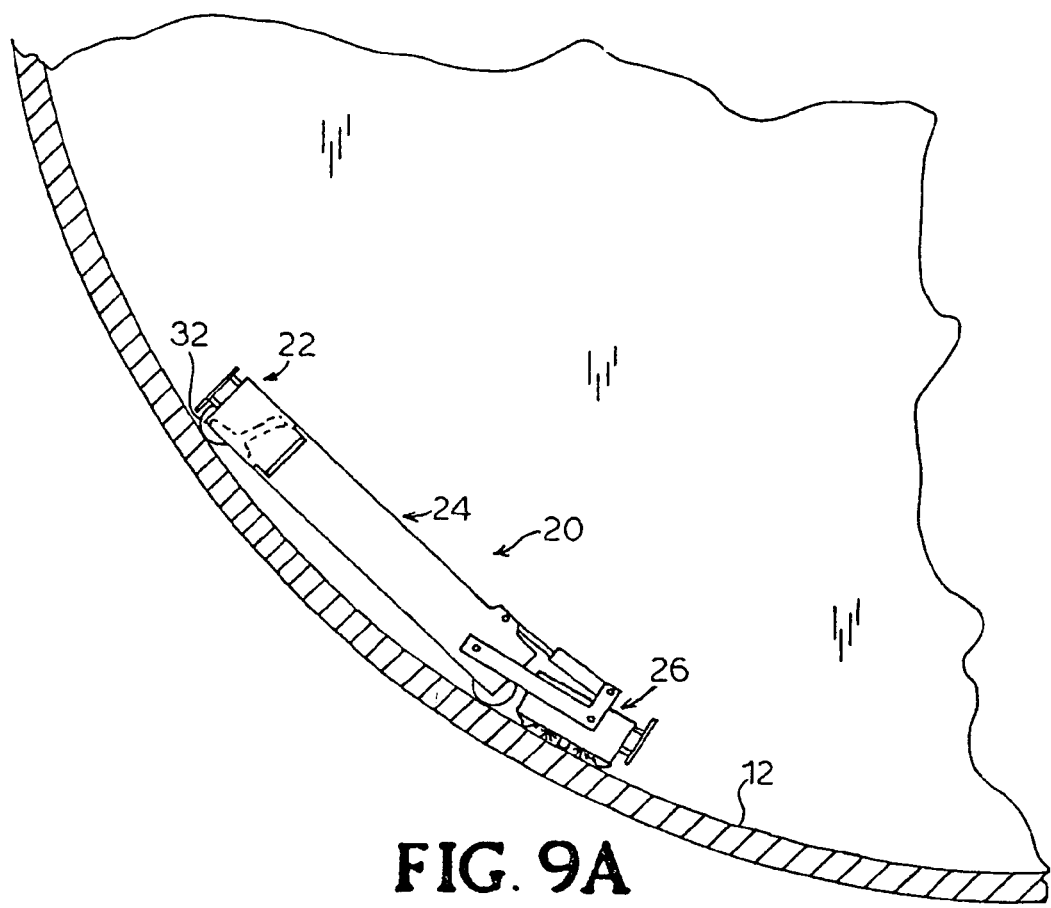
FIG. 9A is a segmented cross sectional view of a tank in which an embodiment of the present invention is traveling circumferentially.
Figure 9B:
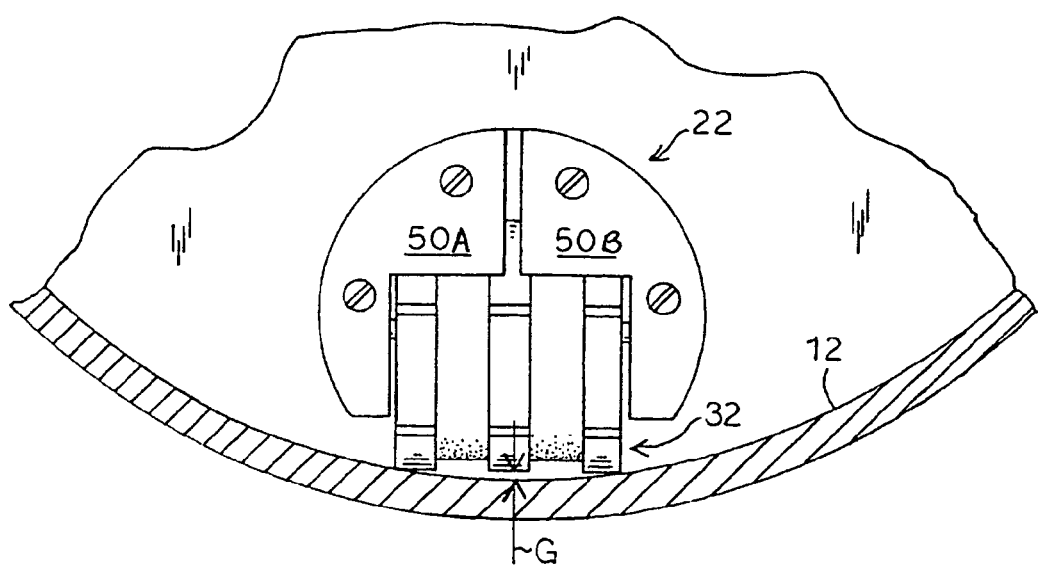
FIG. 9B is a segmented cross sectional view of a tank in which an embodiment of the present invention is traveling along a path parallel to the tank's long axis.

Refer to FIGS. 9A, B. With diameter $D_p$ of outer polar members 74A, B and the inner polar member 76 being substantially equal, all polar members 74A, B, 76 are in contact with the interior surfaces 12, 14A, B of the cylindrical UST 10 in only two relative orientations of the robotic vehicle 20. One orientation occurs when operating on planar tank end plates 14A, B and the other when operating circumferentially on the cylindrical wall 12. When the robotic vehicle 20 operates along a path parallel to the long axis of the UST 10 or on a path at an angle between a "parallel axial" path and a circumferential path, the inner polar member 76 does not contact the surface. The maximum air gap G is typically small between the inner polar member 76 and the surface. Magnetic flux M travels across the gap to attract to a ferrous surface. For example, in the case of the UST 10 having a diameter of 2.4 meters (8 feet), and the front drive polar members (wheels) 74A, B, 76 having a diameter of 5 cm (2 inches) and the length of the shaft 78 5.6 cm (2.2 inches), the maximum air gap G between the periphery of the inner polar member 76 and the tank wall 12 is approximately 0.33 mm (0.013 inches). Larger diameter tanks 10 have a proportionally smaller gap G. In select embodiments of the present invention, the magnetized drive wheeled axle assemblies 32, 42 produce a combined attractive force of 207 lbf. This is sufficient to support a robotic vehicle 20 of about 18 Kg (40 lbs).

Refer to FIGS. 2A, B illustrating a robotic vehicle 20 in assembled condition including three main modules 22, 24, and 26. The power module 24 comprises a forward segment 80 (FIG. 4), a middle segment 90 (FIG. 5), and a rear segment 96 (FIG. 6). In select embodiments of the present invention, each segment 80, 90, 96 is built separately and assembled to the other segments so as to form the integrated power module 24.

Refer to FIG. 4 illustrating the forward segment 80. In select embodiments of the present invention, the forward segment contains an orientation sensor 86 that comprises three mutually orthogonal piezoresistive inclinometers (not shown separately). This type of inclinometer has a flexible beam, typically silicon material, supporting a mass at one end of each inclinometer. Each inclinometer is sensitive along one axis only. As the orientation of the robotic vehicle 20 changes, the mass shifts in relation to the fixed end of the beam, causing the beam to bend. The silicon material changes in electrical resistance in proportion to strain, providing a property that can be readily measured and converted to an orientation reading. By feedback and analysis of signals received from each of the X, Y, and Z inclinometers, the computer 100 determines the yaw, pitch, and roll orientation of the robotic vehicle 20. Similarly, n select embodiments of the present invention, the computer 100 is able to detect a change in direction of the robotic vehicle 20 as it travels the interior of the UST 10.

The transformation mathematics used to relate the inclinometer readings to angular orientation of the robotic vehicle simplify to the following:

Robotic vehicle roll angle=arctan (Y accelerometer reading/Z accelerometer reading).

Robotic vehicle pitch angle=arctan (X accelerometer reading/Z accelerometer reading).

Robotic vehicle yaw angle=arctan (Y accelerometer reading/X accelerometer reading).

In select embodiments of the present invention, the computer 100 uses the calculated information together with data from the odometric encoder in the motor 98 to continuously track the position of the robotic vehicle 20.

The forward segment 80 pivotally connects to the tractor module 22 at a pivot frame 82 with a pin 84. The pin 84 is positioned by any conventional means, such as snap rings (not shown separately) fitted in grooves 84A, B at each end thereof.

Figure 5:
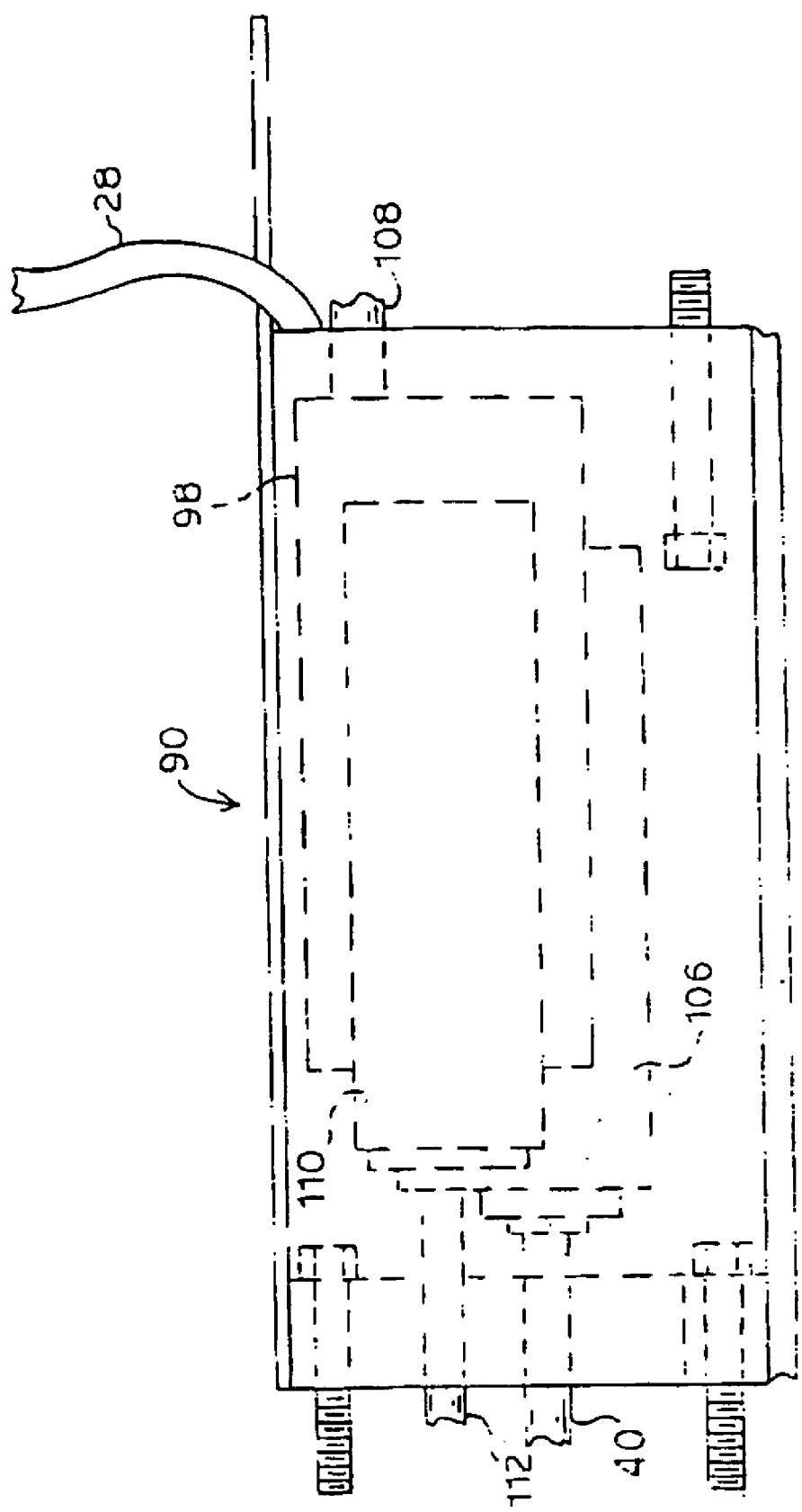
FIG. 5 is a side elevation view of a second segment of the second module of FIG. 2A.

Refer to FIG. 5, illustrating the middle segment 90 of the power module 24. The middle segment 90 communicates with the computer 100 via the tether 28 and contains the motor 110 for generating drive power to the front magnetized drive wheeled axle assembly 32. In addition, the middle segment 90 houses the motor 98 for steering the robotic vehicle 20 and the motor 106 for actuating the transition lever arm 46. On assembly, the middle segment 90 is fastened to the forward segment 80 and the rear segment 96 by appropriate fastening means (not shown separately) to become the power module 24.

Refer to FIG. 6, depicting the rear segment 96 of the power module 24. The rear segment 96 comprises the shaft 108 that is connected at its driven end to the motor 98 (FIG. 5). The shaft 108 mounts the worm gear reducer 102 that, in turn, drives the rear magnetized drive wheeled axle assembly 42 through a set of sprockets 105, 142, and 144 and chain 146. This permits the power module 24 to operate in the same direction and at the same speed as the tractor module 22. Although the front magnetized drive wheeled axle assembly 32 is driven by a first motor 110 and the rear magnetized drive wheeled axle assembly 42 by a second motor 98 the motors 98, 110 are controlled by the computer 100 to operate at the same speed. In select embodiments of the present invention, the motors 98, 110 are servomotors that enable maximum control of speed and direction. The scrapers 104A, B are each mounted with an edge pressed in contact with the rear magnetized drive wheels (not shown separately but of similar configuration to the polar members (wheels) 74A, B, 76 of the front wheeled axle assembly 32) to continuously remove rust particles from the peripheral surfaces thereof. The scrapers 104A, B are oriented in opposite directions so as to accommodate forward and reverse rotation of the rear magnetized drive wheeled axle assembly 42. A pivot shaft 44 extends outwardly from each side of the segment 96 for pivotally connecting the cleaning and inspection module 26.

The shaft 108 mounts a first sprocket 140 that drives a second sprocket 138 via a first chain (not numbered). The second sprocket 138 is mounted coaxially with the worm gear 133 that delivers power to a third sprocket 132 via an intermediate co-axial worm gear (not shown separately) behind the third sprocket 132. A second chain 134 engages the third sprocket 132 and drives a fourth sprocket 136 (FIG. 7) to provide power to the power and cleaning module 26.

In select embodiments of the present invention, the robotic vehicle 20 includes a solenoid-actuated push rod 137, oriented horizontally and positioned above the rear magnetized drive wheeled axle assembly 42 in rear section 96. The push rod 137 is operative to break the magnetic grip of the rear magnetized drive wheeled axle assembly 42 on the surface of the ferrous structure it is contacting.

Figure 10:
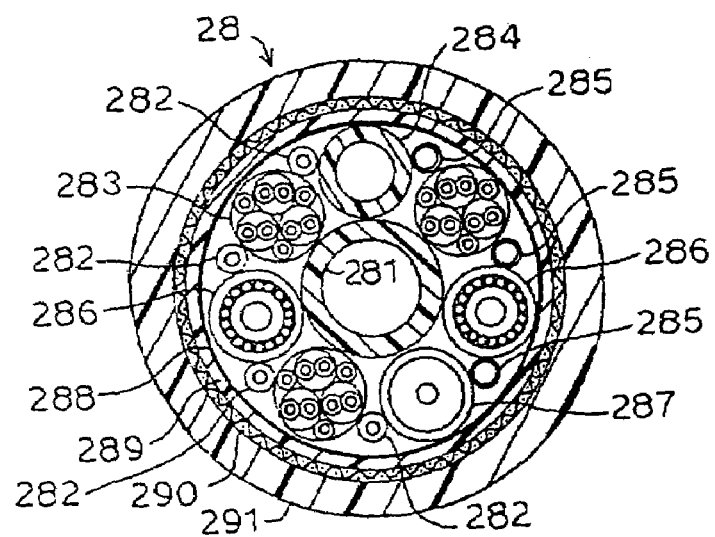
FIG. 10 is an enlarged cross sectional depiction of a tether cable assembly that may be used with an embodiment of the present invention.

Refer to FIGS. 2A, 5 and 10, illustrating the tether 28 connected to the robotic vehicle 20 at the middle segment 90. The tether 28 is formed as an assembly of cables and tubes adapted to perform several functions in communication with the robotic vehicle 20. A cross sectional view of the tether 28 is shown in FIG. 10 and a description and function for each of the components of the tether 28 is listed in the following chart. The tubular core 281 is used to provide a foundation about which to assemble the other components of the tether 28 in a generally cylindrical shape.

In select embodiments of the present invention, the cables and structural components of the tether 28 are as listed in the table below:

| | PART DESCRIPTION | QUANTITY | FUNCTION |
|---|---|---|---|
| 281 | Tubular nylon core | 1 | Couplant fluid/UT block |
| 282 | 24 AWG wire with double outer-wrap served shielding | 4 | Steering and transition motor and sensor power |
| 283 | 3 pairs-28 AWG wire with 0.5 mil polyester tape wrap | 3 | Position signals transmitted |
| 284 | Tubular nylon filler | 1 | Pressurized gas conduit |
| 285 | 20 AWG wire with 0.5 mil polyester tape wrap | 3 | Ground wires |
| 286 | 16 AWG wire with single served shielding | 2 | Drive motor power |
| 287 | 50 (coaxial cable with braided shielding and two layers of 0.5 mil polyester tape wrap at 50% lap) | 1 | Ultrasonic transducer signals |
| 288 | 1.0 mil polyester wrap at 50% lap | 1 | Encasement |
| 289 | HYTREL ® extruded jacket at 20 mils | 1 | Encasement |
| 290 | KEVLAR ® braided jacket | 1 | Encasement |
| 291 | HYTREL ® extruded jacket at 50 mils | 1 | Protection |

(HYTREL® and KEVLAR® are registered trademarks of E.I. duPont de Nemours and Company.) As noted above, the specific function and connection of the cables and tubes comprising the tether 28 are such as to be apparent to those skilled in the trade, and as such are not detailed further.

In select embodiments of the present invention, the tether 28 is involved in the physical deployment into and retrieval of the robotic vehicle 20 from the UST 10; in supplying electric power to perform the motor drive operations, the ultrasonic inspection operation, and transmitting the orientation, travel, and communication signals; and in transmitting signals from the robotic vehicle 20 to the computer 100. In select embodiments of the present invention, the robotic vehicle 20 must drag a length of the tether 28 through the UST 10, at times involving support of its catenary weight as the robotic vehicle 20 traverses the "roof" or end walls of the UST 10. The tether 28 is typically 45 m. (150 ft.) in length. Thus, it is important to keep the weight of the tether 28 at a minimum.

In select embodiments of the present invention, the combination of the tractor module 22 and the power module 24 described above is operative for moving and controlling the movement of the robotic vehicle 20 within the UST 10 by implementation of signals from the computer 100.

Figure 7:
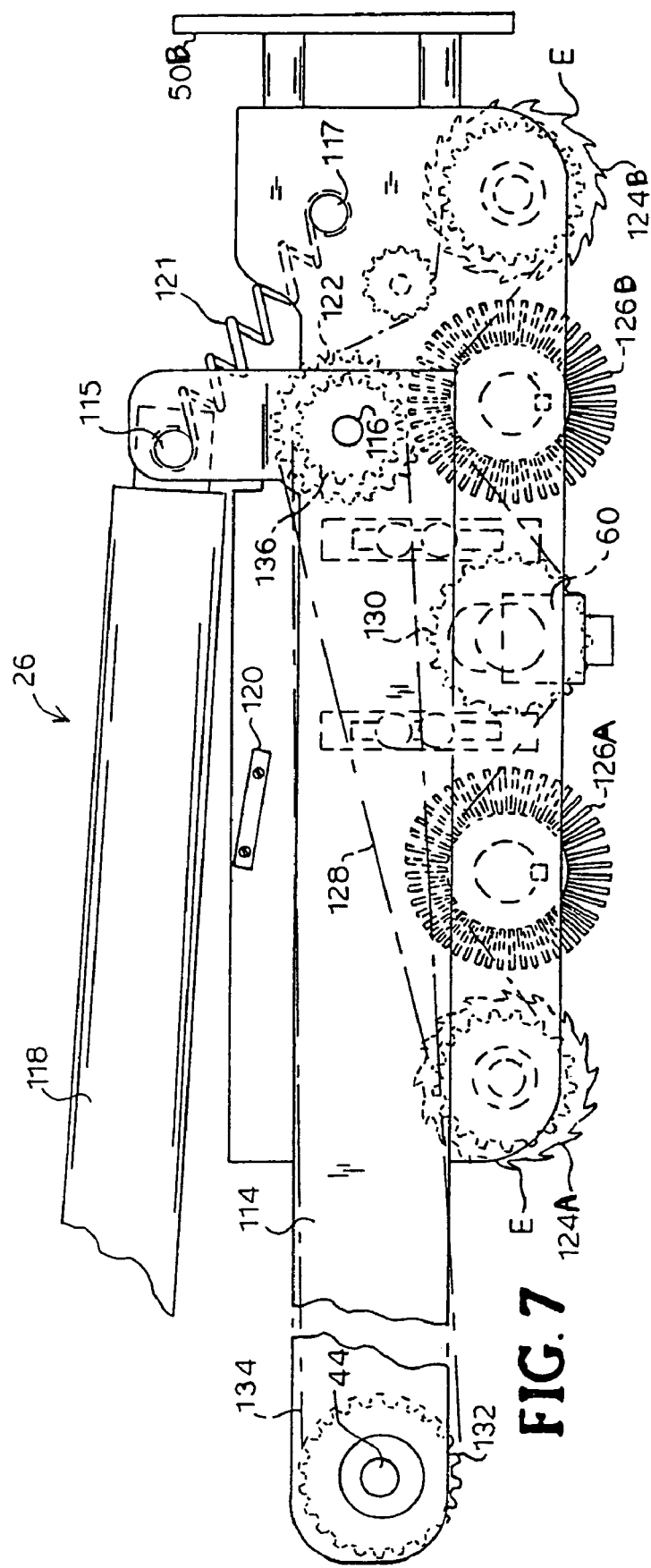
FIG. 7 is a side elevation view of the third module of FIG. 2A.

Refer to FIG. 7. In select embodiments of the present invention, the identification of defects in the walls of a UST 10 is facilitated by the cleaning and inspection module 26.

As described above, the cleaning and inspection module 26 is pivotally connected to the power module 24 at the horizontal pivot pin 44 with a first bar 114 pivotally mounted on either side thereof. The rear portion of each bar 114 is pivotally connected to module 26 at a rear pivot shaft 116, positioned toward the rear portion of cleaning and inspection module 26. The rear pivot shaft 116 mounts the fourth sprocket 136 and the third sprocket 132 involved in the transmission of power for the cleaning and inspection module 26. A pair of telescoping pressurized struts 118, mounted to the shaft 115 at the back ends of the struts 118 and to the power module 24 (FIG. 6) at the front ends of the struts 118, prevents the cleaning and inspection module from moving horizontally while limiting the degree to which the cleaning and inspection module 26 can pivot vertically in relation to the power module 24. In select embodiments of the present invention, the struts 118 are of the telescoping cylinder type and are filled with nitrogen or other substantially inert gas. In select embodiments of the present invention, a supply of pressurized gas (not shown separately) may be connected to the struts 118.

In select embodiments of the present invention as designed above, the cleaning and inspection module 26 is held in contact with the surface on which the robotic vehicle 20 is traveling, regardless of the orientation of the robotic vehicle 20. The stop 120 mounted rigidly to the side of the cleaning and inspection module 26 allows the forward end of the cleaning and inspection module 26 to pivot down to a limited degree with respect to the first bars 114. The tension springs 121 are assembled between the shaft 115 and a selected anchor point 117 on the housing of the cleaning and inspection module 26 to bias the module 26 in the counterclockwise direction in relation to an anchor point 117. This bias pressure, in combination with the operation of the struts 118, assures that the cleaning and inspection module 26 stays in intimate contact with the surface regardless of the orientation of the robotic vehicle 20.

In select embodiments of the present invention, the cleaning and inspection module 26 includes devices for scraping residue off the surface to be inspected. Power is transmitted to the cleaning and inspection module 26 from the third sprocket 132 on the power module 24 via the second chain 134 that is connected at its rear end to the fourth sprocket 136. For the second chain 134 to connect between the pivotally connected power 24 and inspection and cleaning 26 modules, the chain engaging sprockets must be coaxial with the front 44 and rear 116 pivot points for the first bars 114. As illustrated in FIG. 7, the left (or front) end of the first bars 114 are assembled to the front pivot shaft 44 that is positioned in the rear segment 96 of the power module 26 (FIG. 6). In select embodiments of the present invention, the fourth sprocket 136 is commonly mounted with the fifth driving sprocket 122 that is connected to the duplicate cutting wheels 124A, B. The forward cutting wheel 124A and the rear cutting wheel 124B and duplicate rotary brushes 126A, B are connected to the fifth sprocket 122 through a third drive chain 128. The cutting wheels 124A, B are formed with a series of substantially sharp edges E spaced around the diameter thereof and extending across their widths. The cutting wheels 124A, B, especially the sharp edges thereof, are formed preferably of hardened steel or the like. The rotary brushes 126A, B are formed with a series of flexible bristles spaced around the diameter thereof and extending across their widths. In select embodiments of the present invention, the bristles of the brushes 126A, B are of polymeric material. In select embodiments of the present invention, the cutting wheels 124A, B are mounted at the forward and rearmost ends of the cleaning and inspection module 26 and the two rotary brushes 126A, B are mounted therebetween. As illustrated in FIG. 7, the cutting edges E of the forward cutting wheel 124A are angled to cut when the forward cutting wheel 124A rotates in the counterclockwise direction and the cutting edges E of the rear cutting wheel 124B are angled to cut in the clockwise direction. The fifth sprocket 122 drives the cutting wheels 124A, B and the rotary brushes 126A, B via the third drive chain 128.

An idler sprocket 130 is positioned substantially in the center of the third drive chain 128 and is adapted for adjustment to provide chain tension as needed. The third drive chain 128 is entrained in serpentine fashion around a series of sprockets (not shown separately) to cause the forward cutting wheel 124A to rotate in a first direction and the rotary brush 126A to rotate in an opposite direction. The same counter rotation occurs with the rear cutting wheel 124B and the rotary brush 126B. In select embodiments of the present invention, the cutting wheels 124A, B are rotated at a speed about three times faster than the speed of the drive wheeled axle assemblies 32, 42 to effectively remove deposits. In select embodiments of the present invention, to assist the movement of the robotic vehicle 20, the cutting wheels 124A, B operate in the same rotational direction as the drive wheeled axle assemblies 32, 42, albeit faster.

If a cutting wheel rotating in a direction opposite to the direction of travel were to encounter an obstacle such as a weld seam, a jam could occur. To avoid this type of jamming, in select embodiments of the present invention each cutting wheel 124A, B is driven by use of a unidirectional clutch (not shown separately) to enable rotation in the selected drive direction only. In select embodiments of the present invention, a first unidirectional clutch mounted to the front magnetized drive wheeled axle assembly 32 permits rotation thereof only in the counterclockwise direction (FIG. 3B) and a second unidirectional clutch mounted to the rear magnetized drive wheeled axle assembly 42 permits rotation thereof only in the clockwise direction. When the robotic vehicle 20 drives forward, with the tractor module 22 going first, the forward cutting wheel 124A and both rotary brushes 126A, B operate. When the robotic vehicle 20 reverses, i.e., with the tractor module 22 trailing, the motor 110 for driving the front magnetized drive wheeled axle assembly 32 and the motor 98 for driving the rear magnetized drive wheeled axle assembly 42 and the cutting wheels 124A, B are reversed, and the rear cutting wheel 124B and both rotary brushes 126A, B operate. By rotating the rotary brushes 126A, B in the direction opposite to their adjacent respective cutting wheels 124A, B, the particles loosened by the cutting wheels 124A, B are removed from the path of travel of the ultrasonic sensor unit.

In select embodiments of the present invention, one or more ultrasonic transducers (not shown separately) are encapsulated in a block 60 preferably formed of a dense, tough, and resilient material, such as an ultra high molecular weight polyethylene resin. This block 60 is positioned between forward rotary brush 126A and rear rotary brush 126 B. The block 60 is biased downwardly to maintain firm contact with the operating surface for transmitting its sonic signal directly to the surface without having to broach an intervening gap. When the UST 10 is at least partially liquid filled, a lubricant layer exists between the block 60 and at least some of the tank's surface. In select embodiments of the present invention, when the tank is empty, ultrasonic transducer performance is enhanced and the wear on block 60 is minimized via use of a lubricating couplant liquid transmitted through the tube 281 in the tether 28 (FIG. 10).

In select embodiments of the present invention, the ultrasonic transducers are 2-10 MHz pulse echo transducers, adapted for determining wall thickness when coupled with appropriate analytic computer programming therefor. In select embodiments of the present invention, several 10-Mhz ultrasonic transducers are arrayed in a scan path width of about 2.5 cm. (1 inch). In select embodiments of the present invention, ultrasonic data from the transducers are processed with a commercially available program such as that available from INFORMATRICS TESTPRO or the like. In select embodiments of the present invention, the cutting wheels 124A, B and rotary brushes 126A, B operate either in forward or reverse travel of the robotic vehicle 20 and engage the surface ahead of the transducers in the block 60. This ensures a reasonably clean surface for reliable measurements. In select embodiments of the present invention, the ultrasonic transducers may make between approximately 30 and 100 measurements per second. At a speed of approximately 77 mm (3 inches) per second, measurements may be collected about every 0.77-2.6 mm (0.03-0.10 inches).

Refer to FIGS. 11A-11F depicting a robotic vehicle 20 as it progresses in sequential steps from a first surface of the cylindrical wall 12 of an UST 20 to a second surface of a wall or end plate 14A orthogonal thereto.

Figure 11A:
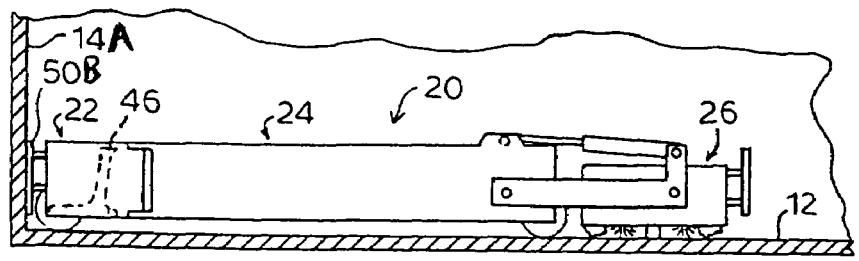
FIGS. 11A-11F show a series of sequential views of an embodiment of the present invention executing a transition from a horizontal surface to a vertical surface of a tank.
Figure 11B:
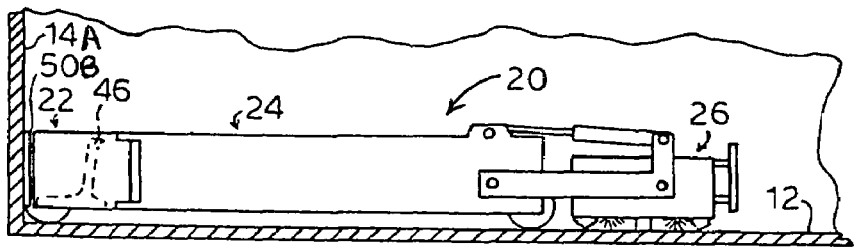
Figure 11C:
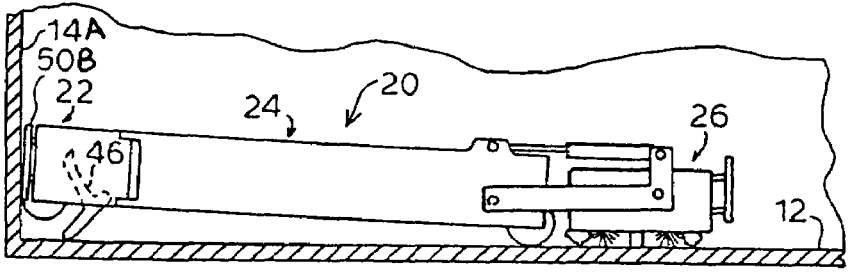

Assume the robotic vehicle 20 is oriented substantially perpendicular to the surface to which it is transferring. Refer to FIG. 11A. Contact sensor 50B and 50A (not shown in FIGS. 11A-D) contacts the end plate 14A of the UST 10. FIG. 11B illustrates a second step in the transition of the robotic vehicle 20 from the cylindrical wall 12 to the end plate 14A in which the robotic vehicle 20 continues to travel and press a leading outer surface of the contact sensors 50A, B against end plate 14A whereby contact sensors 50A, B are telescoped to contact the body of the tractor module 22. A signal, generated by a contact switch (not shown separately) communicating with the contact sensors 50A, B, is transmitted to cause the transition lever arm 46 to pivot downwardly as shown in FIG. 11C. The transition lever arm 46 is pivoted downwardly by movement of the linear actuator 48 as described above. The transition lever arm 46 lifts the forward end of the tractor module 22 off the surface 12. The transition lever arm 46 being connected at the location of the pin 46P (FIGS. 3B, C) moves the robotic vehicle 20 closer to the end plate 14A during its pivoting action so that the front magnetized drive wheeled axle assembly 32 efficiently makes magnetic contact with the end plate 14A. During this transition period, the tractor module 22 is precluded from moving laterally with respect to the other two modules 24, 26. The connection between the cleaning and inspection module 26 and the power module 24 allows relative movement of these two modules 24, 26 in the vertical direction only as depicted in FIGS. 11C-E.

Figure 11D:
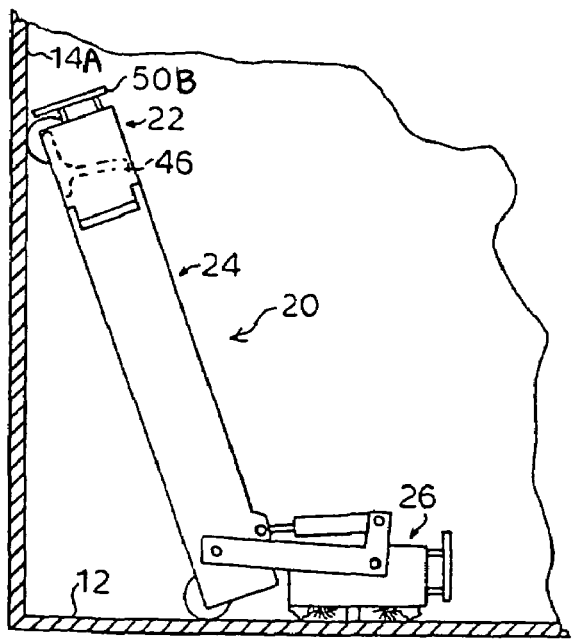
Figure 11E:
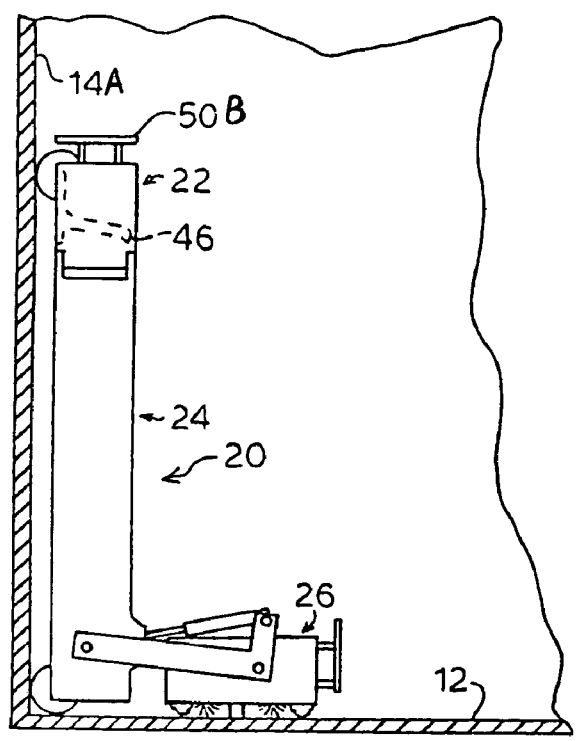

Refer to FIGS. 11C-E. The front magnetized drive wheeled axle assembly 32 powers the front end of the robotic vehicle 20 along the end plate 14A as the rear magnetized drive wheeled axle assembly 42 continues to drive on the cylindrical wall 12, further assisting the robotic vehicle 20 to climb up the end plate 14A. In changing its orientation from horizontal to upwardly angled (FIG. 11D), the contact sensors 50A, B disengage from the end plate 14A and the transition lever arm 46 retracts within the housing of tractor module 22. The mid-point in the transition of the robotic vehicle 20 from the horizontal surface 12 to the vertical surface 14A is illustrated in FIG. 11E, with the robotic vehicle 20 forming a right angle between the power module 24 and the cleaning and inspection module 26. To accommodate the transition between the horizontal surface 12 and the vertical surface 14A, the drive wheeled axle assemblies 32 and 42 are mounted on the robotic vehicle 20 so that a respective forward and rearward portion of the peripheral surface of each wheeled axle assembly 32, 42 extends radially outward from the end of the respective modules 22, 24. The rear push rod 137 (FIG. 6) is positioned perpendicular to the horizontal surface 12. When the solenoid (not shown separately) of the push rod 137 is energized, the rear push rod 137 extends to move the rear magnetized drive wheeled axle assembly 42 away from the horizontal surface 12 facilitating the rear magnetized drive wheeled axle assembly 42 to climb the end plate 14A.

Figure 11F:
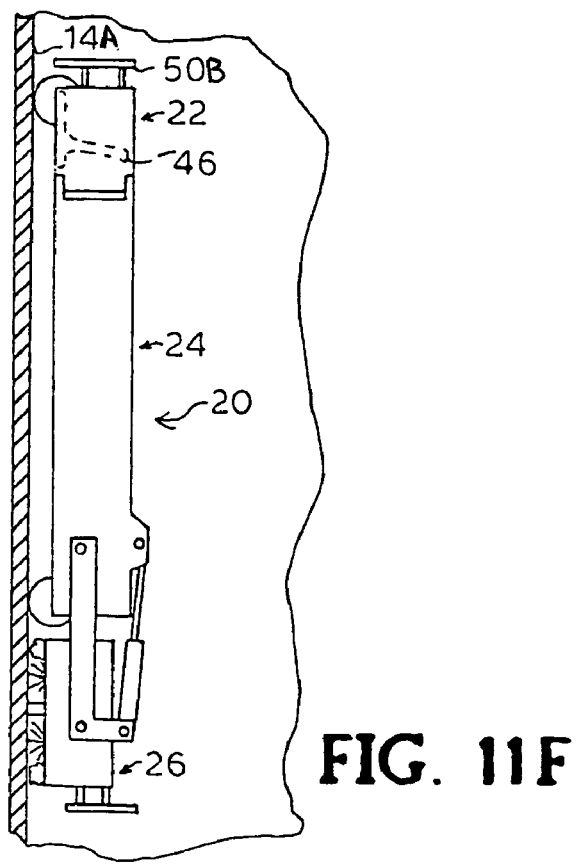

Refer to FIG. 11F, depicting the robotic vehicle 20 after the transition is completed from the horizontal surface 12 to the end plate 14A. In select embodiments of the present invention, the path for inspection of the end plates 14A, B is preferred to follow a series of diametral lines, each being angularly displaced from the previous one. Employing this pattern, the entire surface of each of the end plates 14A, B is inspected.

Figure 12A:
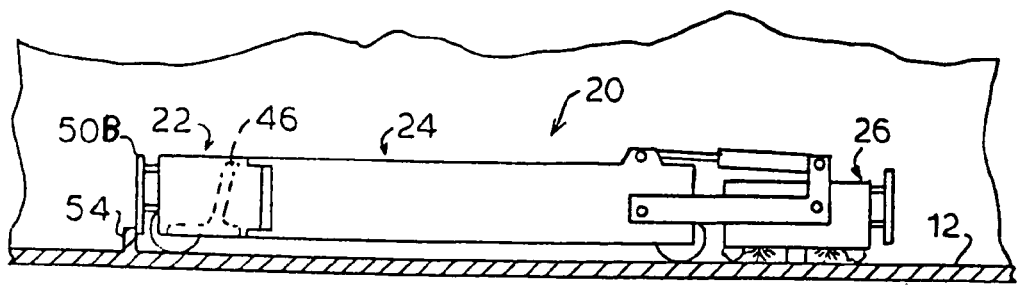
FIGS. 12A-12D show a series of sequential views of an embodiment of the present invention traversing across an obstacle in the tank.
Figure 12B:
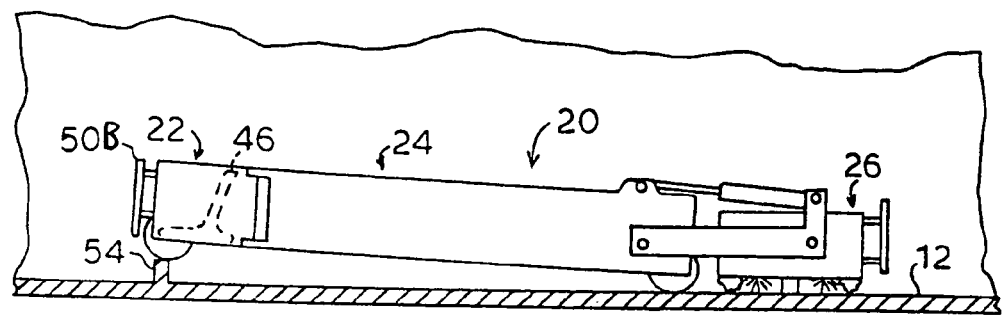
Figure 12C:
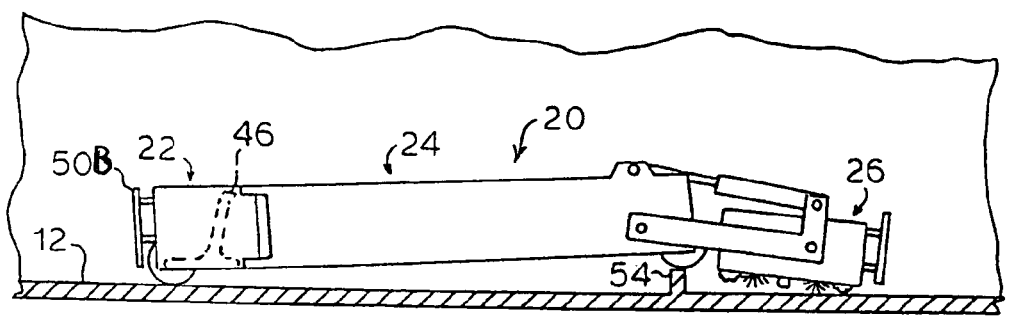
Figure 12D:
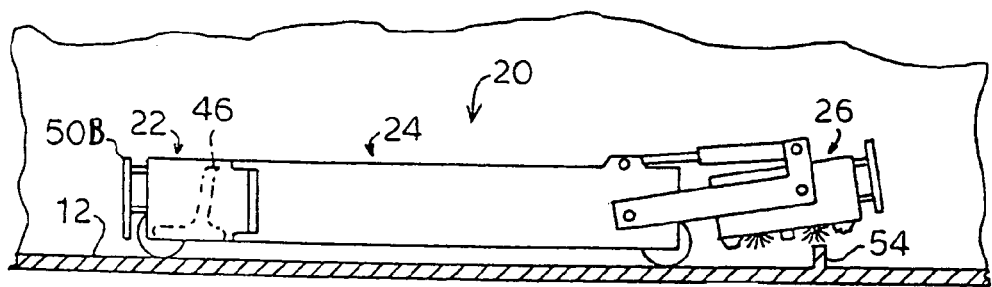

Refer to FIGS. 12A-D. Obstacles encountered within a storage tank include raised seams, wave suppression plates, and internal ribs. FIGS. 12A-D depict the robotic vehicle 20 navigating an obstacle. In select embodiments of the present invention, identification of an obstacle is based on a computer comparison of the known dimensions of an UST 10 with the distance the robotic vehicle 20 has traveled in a straight line since last contacting a perpendicular surface, such as a wall. In FIG. 12A, the contact sensor 50 B contacts the rib 54. As described above for transitioning to another plane of operation, the transition lever 46 is pivoted downwardly and lifts the front of the tractor module 22 up, as shown in FIG. 11C. As the tractor 22 proceeds forward, the front magnetized wheeled axle assembly 32 rolls up onto the rib 54 and the transition lever arm 46 retracts, as shown in FIG. 12B. As depicted in FIG. 12C, when the rear magnetized wheeled axle assembly 42 pushes the robotic vehicle 20, the front magnetized wheeled axel assembly 32 is rolled completely over the rib 54 and is able to roll on the horizontal surface 12 again. The rear magnetized drive wheeled axle assembly 42 continues to drive and to push the robotic vehicle 20 until it hits the rib 54 at which time the front drive wheeled axle assembly is able to assist in pulling the rear drive wheeled axle assembly over the rib 54. Normal driving resumes when both magnetized wheeled axle assemblies 32, 42 are again in contact with the horizontal surface 12 as shown in FIG. 12D, even though the inspection and cleaning module 26 is still being pulled over the rib 54.

Upon initial insertion of the robotic vehicle 20 through the riser 16 into an UST 10, neither the position nor orientation of the robotic vehicle 20 is known to the computer 100. Thus, in select embodiments of the present invention, the robotic vehicle 20 is directed to maneuver through a series of preliminary runs for the purpose of initial orientation and position determination. The robotic vehicle 20 travels first in an arbitrary straight line. Signals generated by its three mutually orthogonal on-board inclinometers are monitored by the computer 100 to determine the shape and slope of the path being traversed. The robotic vehicle 20 is next directed to operate along a horizontal line. At one point, a contact sensor 50A, B on the tractor module 22 contacts a surface approximately perpendicular to the surface on which the robotic vehicle 20 is operating. The computer 100 combines the contact data with stored data on the direction of travel of the robotic vehicle 20 to establish position. Basic position and orientation information is now available for the robotic vehicle 20 to begin inspecting the interior of the UST 10 to evaluate its surface condition and transmit data for the computer 100 to create a record of defects. In select embodiments of the present invention, a preferred path is for the robotic vehicle 20 to travel forward along a first straight line on the cylindrical surface of the wall 12 until it contacts an end plate 14A, B, then reverse direction to travel backward to the opposite end plate 14A, B along a line that is substantially parallel to and slightly offset from the previous path. When the entire process of tank inspection has been completed, the robotic vehicle 20 is lifted from the UST 10 by the tether 28 to a position near the riser 16 through which it entered. In select embodiments of the present invention, the tether 28 is connected to the robotic vehicle 20 causing the back of the robotic vehicle 20 to tip up. The back of the robotic vehicle 20 is fitted with a retrieval bar (not shown separately) adapted for engaging by a retrieval hook (not shown separately) for removing the robotic vehicle 20 from the UST 10.

Figure 13:
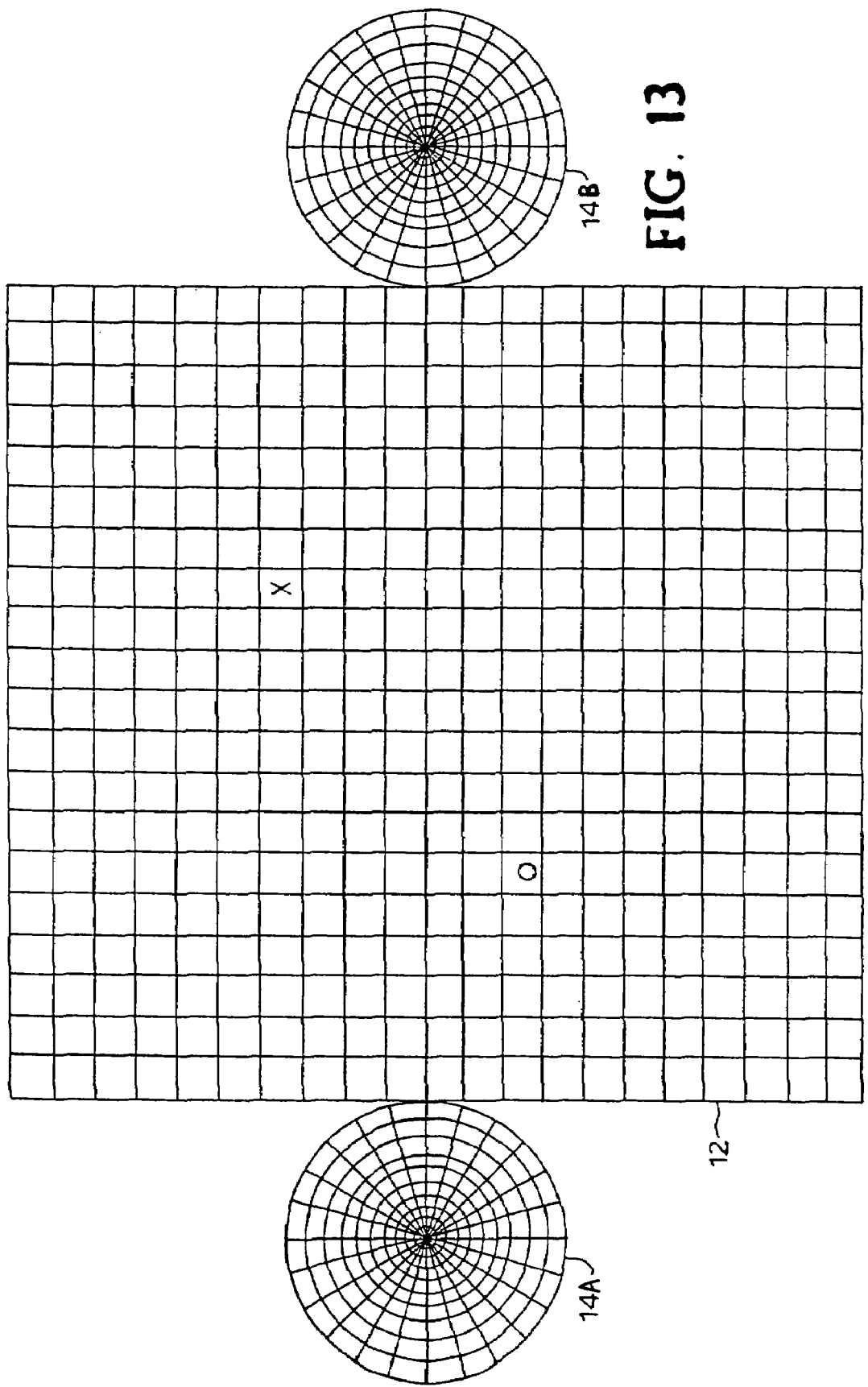
FIG. 13 is a planar graphical map of the interior surface of the tank being inspected with indications of the positions of an embodiment of the present invention and a tank wall defect shown on a grid.

Refer to FIG. 13 depicting a flat projected map of the interior surface of the UST 10. The map includes the unfurled surface of the cylindrical wall 12 and the end plates 14A, B, each divided by reference grid lines. In select embodiments of the present invention, the surface of the cylindrical wall 12 is marked by square grid lines and the surface of the end plates 14A, B by radial grid lines. The generation of these grids and plotting of the position of the robotic vehicle 20 thereon are accomplished through a mapping program loaded on the computer 100. For illustration, points locating defects of an UST 10 are marked with an "X" on the map of FIG. 13, whereas the present location of the robotic vehicle 20 is marked by a small circle.

Figure 14:
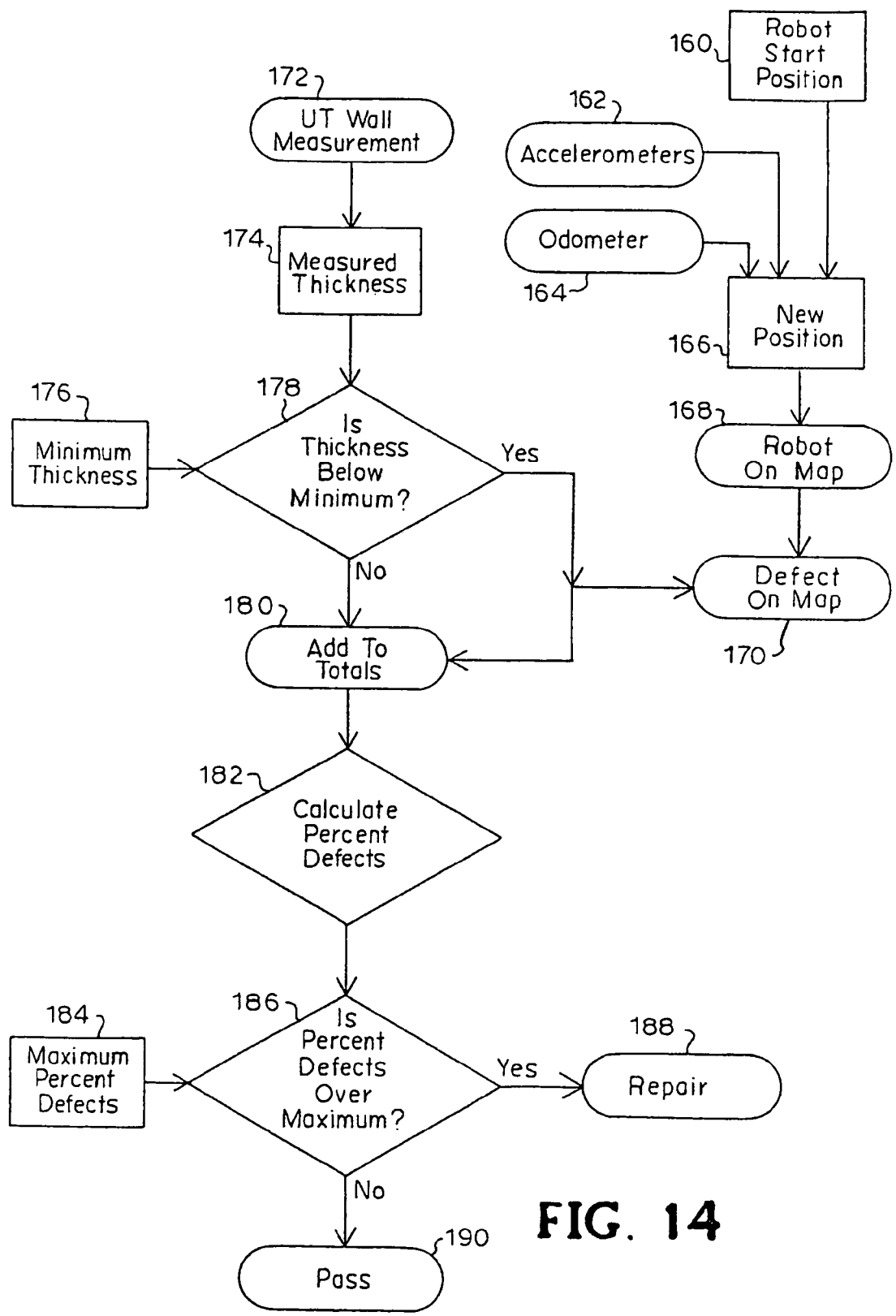
FIG. 14 is a diagrammatic flow chart of a computer program for indication of the positions of tank wall defects on the graphical map of FIG. 13.

Refer to FIG. 14, a flow chart on the operation of the mapping function of select embodiments of the present invention. The location of the robotic vehicle 20 within a UST 10 is determined by combining a start position 160 with data obtained from the on-board inclinometers 162 and the encoder-odometer 164. These data provide a new position 166 that is marked 168 with a temporary designation, such as the "X" shown on the map of FIG. 13. Measurements of the wall thickness are generated constantly by the ultrasonic transducers in the block 60. The ultrasonic transducer wall measurement 172 is taken to derive a measured thickness 174 as an input to a determination 178 that compares the measurement 174 with a minimum thickness 176. If the measured thickness is below the minimum, the temporary position "X" is made permanent as a defect 170 for establishing in a record 180 of defect locations. Whether the measured thickness is below or within tolerance, it is added to the accumulating total (record) 180 of measurements taken. This enable a determination of percentage defects 182. A final test is a comparison 186 of the calculated percent defects with an established maximum percentage allowed 184, the results of which if positive invokes a request for repair 188, and if negative, a pass 190 with no required remediation.

In select embodiments of the present invention, the robotic vehicle 20 may be manipulated autonomously by a computer 100 or by an operator controlling the robotic vehicle 20, or both. Operator control is preferable if the environment being traversed is unknown and potential risk indicates need for an informed immediate decision. In known environments, an automated program involving initial orientation of the robotic vehicle followed by a pre-scribed pattern of navigating is warranted. Programmed control of the robotic vehicle is most practical in cases of repeat inspections of known devices.

Accordingly, all such modifications are intended to be included within the scope of this invention as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The abstract of the disclosure is provided to comply with the rules requiring an abstract that will allow a searcher to quickly ascertain the subject matter of the technical disclosure of any patent issued from this disclosure. It is submitted with the understanding that it will not be used to interpret or limit the scope or meaning of the claims. 37 CFR § 1.72 (b). Any advantages and benefits described may not apply to all embodiments of the invention.

We claim:

1. A system facilitating access to ferrous surfaces of a structure, said system comprising:

motors:

at least one conveyance having a long axis about which sections of said conveyance articulates, said conveyance having at least three said sections operably connected as at least a front section to a middle section and as said middle section to a rear section in line along the long axis of said conveyance, wherein said conveyance is deployed upon said ferrous surfaces without either modifying said structure or expanding access to said structure, and wherein said front section turns in only a first plane with respect to said middle section and said rear section turns in only a second plane with respect to said middle section, and wherein said front section incorporates a first part of a first connection assembly for connection to said middle section, at least one first magnetic wheeled axle assembly comprising polar member wheels and first sets of annular permanent magnets and at least one first pivotable lever arm, each said first set of annular permanent magnets comprising at least two annular permanent magnets, and wherein said front section steers said conveyance and transfers to the surface of operation at least part of the power to propel said conveyance, and wherein said middle section incorporates at least one second magnetic wheeled axle assembly comprising polar member wheels and second sets of annular permanent magnets, each said second set of annular permanent magnets comprising at least two annular permanent magnets, a second part of said first connection assembly for connection to said front section, a first part of a second connection assembly for connection to said rear section, at least one of said motors incorporating interoperable connections to at least one device in each of said front, middle and rear sections and at least one first push rod, and wherein said rear section incorporates a second part of said second connection assembly for connection to said middle section, and at least one abrading device, and wherein said rear section turns to permit changing the plane of operation of said conveyance only if each of said front, middle and rear sections are at least approximately aligned along the centerline of said long axis of said conveyance, and wherein said conveyance can move to a surface of operation in a plane different from the plane of the surface of current operation only in a forward direction such that said front section is moved to a new surface of operation prior to said middle and rear sections;

at least one tether in operable communication with said conveyance, wherein said tether incorporates at least means for distributing power, means for distributing control signals and means for distributing fluids to said conveyance;

at least one control system in operable communication with at least said means for distributing control signals, at least part of which said control system is remote from said conveyance and in operable communication with said conveyance via said means for distributing control signals, wherein said control system is in operable communication with at least one power source external to said conveyance, and wherein said power source energizes said motors; and sensors, wherein said sensors facilitate at least navigation and inspection functions.

2. The system of claim 1 in which said first plane is parallel to the surface upon which said front section is moving and said second plane is perpendicular to the surface upon which said front section is moving, wherein said rear section turns only in one direction and only for purposes of permitting said conveyance to change planes of operation.

3. The system of claim 2 in which said conveyance responds to input from at least one first contact switch in operable communication with a first pair of said sensors, wherein said first pair of sensors are mounted on first telescoping mounts that are parallel to the front of said front section, said first telescoping mounts compressing uniformly upon contact with a surface that is approximately perpendicular to the surface of operation of said conveyance.

4. The system of claim 3 in which a second pair of said sensors is mounted on a second telescoping mount that is parallel to the back of said rear section, said second telescoping mount compressing uniformly upon contact with a surface that is approximately perpendicular to the surface of operation of said conveyance, said compression activating at least one second contact switch, wherein activating said second contact switch alerts said conveyance to the need to alter course.

5. The system of claim 1 in which at least one of said motors is a DC reversible servomotor and in which at least one said DC reversible servomotor incorporates at least one odometric encoder.

6. The system of claim 1 in which said abrading device is selected from the group consisting of rotatable brushes, rotatable cutting wheels, scrapers, and combinations thereof, wherein said rotatable brushes and said rotatable cutting wheels are powered by at least one of said motors.

7. The system of claim 6 in which said scrapers are employed as pairs of said scrapers, mounted adjacent the outer circumference of each of said polar member wheels, wherein said pairs of scrapers serve to remove debris that accumulates on said polar member wheels, and wherein a first scraper of said scrapers in each said pair of said scrapers is mounted to remove debris when said conveyance is moving in a first direction and a second scraper of said scrapers in each said pair of said scrapers is mounted to remove debris when said conveyance is moving in a direction opposite to said first direction.

8. The system of claim 1 in which said abrading device comprises at least one first rotatable cylindrical brush coaxially mounted on said rear section to be approximately parallel to, and approximately the same width as, said second wheeled axle assembly.

9. The system of claim 8 in which said abrading device further comprises at least one first rotatable cylindrical cutting wheel coaxially mounted on said rear section to be approximately parallel to, and approximately the same width as, said second wheeled axle assembly, wherein said first cutting wheel rotates in the direction of movement of said conveyance and is protected by a unidirectional clutch.

10. The system of claim 9 in which said abrading device further comprises said at least one first cylindrical rotatable cutting wheel cooperating with said at least one first rotatable cylindrical brush in a cooperating pair, wherein said cooperating pair is mounted across the width of said rear section, said width perpendicular to said long axis, so as to be parallel to the plane of operation of said conveyance, and wherein said cooperating pair is approximately the same width as said second wheeled axle assembly.

11. The system of claim 10 in which said abrading device comprises a first and second said cooperating pair, wherein said first rotatable cylindrical brush and said first cylindrical rotatable cutting wheel of said first cooperating pair are rotated upon said conveyance moving in a first direction, said first rotatable cylindrical brush rotating counter to the rotation direction of said first cylindrical rotatable cutting wheel, and wherein a second rotatable cylindrical brush and a second cylindrical rotatable cutting wheel of said second cooperating pair are rotated upon said conveyance moving in a second direction opposite to said first direction, said second rotatable cylindrical brush rotating in a direction counter to the rotation direction of said second cylindrical rotatable cutting wheel.

12. The system of claim 1 in which each said first and second magnetic wheeled axle assemblies comprises at least three said polar member wheels of a first diameter coaxially mounted parallel one to the other and in which each said first and second sets of annular permanent magnets comprises at least two said annular permanent magnets of a second diameter smaller than said first diameter, wherein each said annular permanent magnet of each said first and second sets set of annular permanent magnets is mounted coaxially so as to separate each of said polar member wheels from another of said polar member wheels, and wherein any two said annular permanent magnets, as affixed on either side of a polar member wheel, are oriented with opposing polarities.

13. The system of claim 12 in which at least one of said polar member wheels of a first diameter incorporates grooves across the width of the outer circumference of said at least one polar member wheel of a first diameter, wherein said grooves enhance fraction.

14. The system of claim 1 in which said conveyance is portable and configurable to insert into a riser of an underground tank.

15. The system of claim 14 in which said conveyance weighs less than about 18 Kg (40 lbs) and is configurable to have a diameter perpendicular to said long axis thereof of less than about 10 cm (4.0 inches) to permit insertion of said conveyance into said riser.

16. The system of claim 1 in which:
said front section further comprises:
  three said polar member wheels and two said annular permanent magnets;
  at least a first steering mechanism for orienting said front section in a single plane;
  wherein orienting said front section in said single plane also orients said conveyance, and
  wherein said pivotally mounted first lever arm operates on said front section to lift said front section from a first surface upon which said first wheeled axle assembly is resting and lower said first wheeled axle assembly to rest upon a surface different from said first surface; and
  first communicating assemblies to facilitate operation of said first wheeled axle assembly, said first lever arm and said steering mechanism;
said middle section further comprises:
  three said polar member wheels and two said annular permanent magnets in said second sets of annular permanent magnets;
  at least one of said motors;
  at least a first part of a maneuvering assembly;
  second communicating assemblies in operable communication at least with some said first communicating assemblies;
  third communicating assemblies in operable communication with at least said second wheeled axle assembly; and
  fourth communicating assemblies in operable communication with at least some parts of said middle and rear sections; and
said rear section further comprises:
  at least a second part of said maneuvering assembly,
  wherein said maneuvering assembly permits said rear section to turn to follow said middle section onto a surface in a plane of operation different from a plane of operation in which said rear section is operating currently;
  at least one biasing mechanism,
  wherein said biasing mechanism permits said rear section to maintain firm contact with said surface of operation regardless of the orientation of said conveyance; and
  fifth communicating assemblies in operable communication with at least some of said fourth communicating assemblies to facilitate at least the operation of said abrading device.

17. The system of claim 1 in which said tether comprises a flexible hollow conduit environmentally sealed at least at the juncture with said conveyance and suitable for containing items selected from the group consisting of: cables, tubes, tubular nylon core, tubular nylon filler, coaxial cable, extruded jackets, braided jackets, insulated copper wire, wire, hose, pressurized hose, and combinations thereof.

18. The system of claim 1 in which said sensors are selected from the group consisting essentially of: acoustic sensors, ultrasonic transducers, electrical sensors, piezoresistive sensors, attitude sensors, contact sensors, thickness sensors, inclinometers, mutually orthogonal inclinometers, and combinations thereof,
wherein at least one of said sensors is encapsulated in a block of dense, tough and resilient material suitable for continuously contacting said surface of operation while said conveyance is moving.

19. The system of claim 1 in which said control system further comprises:
  at least one personal computer,
  wherein said computer is interfaced to said conveyance via at least one means of communication carried in said tether, and
  wherein said computer facilitates control of said conveyance, positioning of said conveyance, mapping of said surfaces, assessment of said surfaces, and defect identification and location upon said surfaces;
  a supply of pressurized inert gas,
  wherein said supply is interfaced to said conveyance via at least one means for supplying material carried in said tether, and
  wherein said power source external to said conveyance supplies at least electrical power to said conveyance via at least an interface to means for supplying power carried in said tether;
  at least one transceiver incorporated in at least one said sections of said conveyance,
  wherein said transceiver communicates between at least said conveyance and at least said computer; and
  at least one retrieval bar affixed to said rear section of said conveyance,
  wherein said retrieval bar facilitates recovery of said conveyance from confined locations.

20. The system of claim 1 in which at least a part of at least one said sections of said conveyance is sealed and pressurized with an inert gas.

* * * * *